US008340743B2

(12) United States Patent
Jenkins et al.

(10) Patent No.: US 8,340,743 B2
(45) Date of Patent: Dec. 25, 2012

(54) METHODS, SYSTEMS AND COMPUTER PROGRAM PRODUCTS FOR POSITIONING A GUIDANCE APPARATUS RELATIVE TO A PATIENT

(75) Inventors: Kimble Jenkins, Memphis, TN (US); David D. Beatty, Raleigh, NC (US)

(73) Assignee: MRI Interventions, Inc., Memphis, TN (US)

( * ) Notice: Subject to any disclaimer, the term of this patent is extended or adjusted under 35 U.S.C. 154(b) by 898 days.

(21) Appl. No.: 12/273,827

(22) Filed: Nov. 19, 2008

(65) Prior Publication Data

US 2009/0131783 A1    May 21, 2009

Related U.S. Application Data

(60) Provisional application No. 60/989,525, filed on Nov. 21, 2007.

(51) Int. Cl.
*A61B 5/05* (2006.01)
(52) U.S. Cl. .......................... 600/429; 600/424; 600/425
(58) Field of Classification Search .......... 600/407–429; 606/130
See application file for complete search history.

(56) References Cited

U.S. PATENT DOCUMENTS

| 4,319,136 A | 3/1982 | Jinkins |
| 4,386,602 A | 6/1983 | Sheldon et al. |
| 4,838,265 A | 6/1989 | Cosman et al. |
| 5,125,888 A | 6/1992 | Howard et al. |
| 5,154,723 A | 10/1992 | Kubota et al. |
| 5,342,356 A | 8/1994 | Ellman et al. |
| 5,469,847 A | 11/1995 | Zinreich et al. |
| 5,638,819 A | 6/1997 | Manwaring et al. |
| 5,655,084 A | 8/1997 | Pinsky et al. |
| 5,695,501 A | 12/1997 | Carol et al. |
| 5,699,801 A | 12/1997 | Atalar et al. |
| 5,707,335 A | 1/1998 | Howard et al. |
| 5,728,079 A | 3/1998 | Weber et al. |
| 5,776,144 A | 7/1998 | Leysieffer et al. |
| 5,779,694 A | 7/1998 | Howard et al. |

(Continued)

FOREIGN PATENT DOCUMENTS

DE    196 25 834 A1    1/1998

(Continued)

OTHER PUBLICATIONS

Baker et al., Neurostimulation systems: assessment of magnetic field interactions associated with 1.5- and 3-Tesla MR systems, J Magn Reson Imaging, 2005, 72-77, 21(1).

(Continued)

*Primary Examiner* — Sanjay Cattungal
(74) *Attorney, Agent, or Firm* — Myers Bigel Sibley & Sajovec, PA

(57) ABSTRACT

A method for positioning a guide device for placement of an interventional object in a body, the guide device having a guide axis, includes: determining a target point in the body and a reference point, wherein the target point and the reference point define a planned trajectory line (PTL) extending through each; determining a visualization plane, wherein the PTL intersects the visualization plane at a sighting point; mounting the guide device relative to the body to move with respect to the PTL, wherein the guide device does not intersect the visualization plane; determining a point of intersection (GPP) between the guide axis and the visualization plane; and aligning the GPP with the sighting point in the visualization plane.

13 Claims, 15 Drawing Sheets

U.S. PATENT DOCUMENTS

| | | | |
|---|---|---|---|
| 5,928,145 | A | 7/1999 | Ocali et al. |
| 5,993,463 | A | 11/1999 | Truwit |
| 6,006,126 | A | 12/1999 | Cosman |
| 6,050,992 | A | 4/2000 | Nichols |
| 6,064,904 | A | 5/2000 | Yanof et al. |
| 6,119,032 | A | 9/2000 | Martin et al. |
| 6,167,292 | A | 12/2000 | Badano et al. |
| 6,167,311 | A | 12/2000 | Rezai |
| 6,195,577 | B1* | 2/2001 | Truwit et al. ............ 600/411 |
| 6,206,890 | B1 | 3/2001 | Truwit |
| 6,216,030 | B1 | 4/2001 | Howard et al. |
| 6,263,229 | B1 | 7/2001 | Atalar et al. |
| 6,267,769 | B1 | 7/2001 | Truwit |
| 6,267,770 | B1 | 7/2001 | Truwit |
| 6,273,896 | B1 | 8/2001 | Franck et al. |
| 6,282,437 | B1 | 8/2001 | Franck et al. |
| 6,284,971 | B1 | 9/2001 | Atalar et al. |
| 6,298,262 | B1 | 10/2001 | Franck et al. |
| 6,351,662 | B1 | 2/2002 | Franck et al. |
| 6,356,786 | B1 | 3/2002 | Rezai et al. |
| 6,368,329 | B1 | 4/2002 | Truwit |
| 6,405,079 | B1 | 6/2002 | Ansarinia |
| 6,419,680 | B1 | 7/2002 | Cosman |
| 6,438,423 | B1 | 8/2002 | Rezai et al. |
| 6,526,318 | B1 | 2/2003 | Ansarinia |
| 6,529,765 | B1* | 3/2003 | Franck et al. ............ 600/427 |
| 6,539,263 | B1 | 3/2003 | Schiff et al. |
| 6,584,351 | B1 | 6/2003 | Ekwall |
| 6,606,513 | B2 | 8/2003 | Lardo et al. |
| 6,609,030 | B1 | 8/2003 | Rezai et al. |
| 6,628,980 | B2 | 9/2003 | Atalar et al. |
| 6,675,033 | B1 | 1/2004 | Lardo et al. |
| 6,701,176 | B1* | 3/2004 | Halperin et al. ........ 600/411 |
| 6,708,064 | B2 | 3/2004 | Rezai |
| 6,725,092 | B2 | 4/2004 | MacDonald et al. |
| 6,752,812 | B1 | 6/2004 | Truwit |
| 6,772,000 | B2 | 8/2004 | Talpade |
| 6,782,288 | B2* | 8/2004 | Truwit et al. ............ 600/429 |
| 6,904,307 | B2 | 6/2005 | Karmarkar et al. |
| 6,920,347 | B2 | 7/2005 | Simon et al. |
| 7,155,316 | B2 | 12/2006 | Sutherland et al. |
| 7,167,760 | B2 | 1/2007 | Dawant et al. |
| 7,217,276 | B2 | 5/2007 | Henderson et al. |
| 7,235,084 | B2 | 6/2007 | Skakoon et al. |
| 7,241,283 | B2 | 7/2007 | Putz |
| 2001/0004676 | A1 | 6/2001 | Ouchi |
| 2001/0014771 | A1* | 8/2001 | Truwit et al. ............ 600/417 |
| 2001/0053879 | A1 | 12/2001 | Mills et al. |
| 2002/0010479 | A1 | 1/2002 | Skakoon et al. |
| 2002/0019641 | A1 | 2/2002 | Truwit |
| 2002/0049451 | A1 | 4/2002 | Parmer et al. |
| 2002/0052610 | A1 | 5/2002 | Skakoon et al. |
| 2003/0028095 | A1 | 2/2003 | Tulley et al. |
| 2003/0050557 | A1 | 3/2003 | Susil et al. |
| 2003/0055436 | A1 | 3/2003 | Daum et al. |
| 2003/0120143 | A1 | 6/2003 | Franklin et al. |
| 2004/0046557 | A1 | 3/2004 | Karmarkar et al. |
| 2004/0064148 | A1 | 4/2004 | Daum et al. |
| 2004/0092810 | A1 | 5/2004 | Daum et al. |
| 2004/0167543 | A1 | 8/2004 | Mazzocchi et al. |
| 2004/0215279 | A1 | 10/2004 | Houben et al. |
| 2004/0228796 | A1 | 11/2004 | Talpade |
| 2004/0267284 | A1 | 12/2004 | Parmer et al. |
| 2005/0070781 | A1 | 3/2005 | Dawant et al. |
| 2005/0222647 | A1 | 10/2005 | Wahlstrand et al. |
| 2005/0251030 | A1* | 11/2005 | Azar et al. ............ 600/429 |
| 2006/0192319 | A1 | 8/2006 | Solar |
| 2006/0195119 | A1 | 8/2006 | Mazzocchi et al. |
| 2006/0229641 | A1* | 10/2006 | Gupta et al. ............ 606/130 |
| 2006/0252314 | A1 | 11/2006 | Atalar et al. |
| 2007/0064739 | A1* | 3/2007 | Krishnamachari ........ 370/486 |
| 2007/0106305 | A1 | 5/2007 | Kao et al. |
| 2007/0118049 | A1 | 5/2007 | Viola |
| 2008/0039709 | A1 | 2/2008 | Karmarkar |
| 2008/0306375 | A1* | 12/2008 | Sayler et al. ............ 600/417 |
| 2009/0082783 | A1* | 3/2009 | Piferi ............ 606/130 |
| 2009/0112082 | A1* | 4/2009 | Piferi et al. ............ 600/411 |
| 2009/0112084 | A1* | 4/2009 | Piferi et al. ............ 600/421 |
| 2009/0118610 | A1* | 5/2009 | Karmarkar et al. ........ 600/420 |
| 2009/0171184 | A1* | 7/2009 | Jenkins et al. ............ 600/411 |
| 2009/0177077 | A1* | 7/2009 | Piferi et al. ............ 600/414 |

FOREIGN PATENT DOCUMENTS

| | | |
|---|---|---|
| DE | 100 29 736 A1 | 3/2002 |
| DE | 100 29 737 A1 | 5/2003 |
| EP | 1 524 626 A | 4/2005 |
| WO | WO 98/52064 | 11/1998 |
| WO | WO 03/102614 | 12/2003 |
| WO | WO 2004/029782 | 4/2004 |
| WO | WO 2004/058086 | 6/2004 |
| WO | WO 2006/081409 | 8/2006 |
| WO | WO 2006/099475 | 9/2006 |
| WO | WO 2007/064739 | 6/2007 |
| WO | WO 2007/106558 | 9/2007 |

OTHER PUBLICATIONS

Bhidayasiri et al., Bilateral neurostimulation systems used for deep brain stimulation: In vitro study of MRI-related heating at 1.5 T and implications for clinical imaging of the brain, Magn Reson Imaging, 2005, 549-555, 23(4).

Buchli et al., Increased RF power absorption in MR imaging due to RF coupling between body coil and surface coil, Magn Reson Med, 1989, 105-112, 9(1).

Chou et al., RF heating of implanted spinal fusion stimulator during magnetic resonance imaging, IEEE Trans Biomed Eng, 1997, 367-373, 44(5).

Dorward et al., Accuracy of true frameless stereotaxy: In vivo measurement and laboratory phantom studies, J. Neurosurg., 1999, 90:160-168.

Francel, Nexframe System, Bilateral Active Lead Delivery to STN Using Nexframe, Oklahoma University Presbyterian Hospital, Image-Guided Neurolgics.

Grimson et al., An automatic registration method for frameless stereotaxy, image guided surgery, and visualization, IEEE Tran on Medical Imaging, Apr. 1996, 129-140.

Hall et al., Brian biopsy sampling by using prospective stereotaxis and a trajectory guide, J. Neurosurg., 2001, 94:67-71.

Jorgensen, Erik, Brain Image Analsis Team Joins SCI Institute, http://www.sci.utah.edu/stories/2007/Gerig_NeuroimageAnalysis.html, (2007), 3 Pages.

Ladd et al., Reduction of resonant RF heating in intravascular catheters using coaxial chokes, Magn Reson Med, 2000, 615-619, 43(4).

Lin et al., "A Wavelet-Based Approximation of Surface Coil Sensitivity Profiles for Correction of Image Intensity Inhomogeneity and Parallel Imaging Reconstruction," *Human Brain Mapping* 2003, 19(2):96-111.

Liu et al., Remotely-Controlled Approach for Stereotactic Neurobiopsy, Computer Aided Surgery, 2002, 7:237-247.

Luechinger et al., In vivo heating of pacemaker leads during magnetic resonance imaging, Eur Heart J, 2005, 376-383, 26(4).

Martin, Can cardiac pacemakers and magnetic resonance imaging systems co-exist?, Eur Heart J, 2005, 325-327, 26(4).

Martin et al., Placement of Deep Brain Stimulator Electrodes Using Real-Time High-Field Interventional Magnetic Resonance Imaging, Magnetic Resonance in Medicine, 2005, 54:1107-1114.

Rezai et al., Neurostimulators: potential for excessive heating of deep brain stimulation electrodes during magnetic resonance imaging, J Magn Reson Imaging, 2001, 488-489, 14(4).

Sauser, Brittany, A 3-D View of the Brain, http://www.technologyreview.com/Biotech/19140, Aug. 6, 2007, 3 Pages.

Singh et al., "Accurate Intensity Correction for Endorectal Surface Coil MR Imaging of the Prostate," IEEE Transactions on Nuclear Science, 1993, 40(4):1169-1173.

Smith et al., The Neurostation—A Highly Accurate, Minimally Invasive Solution to Frameless Stereotactic Neurosurgery, Computerized Medical Imaging and Graphics, 1994, 247-256, 18(4).

STarFix™—Dr. Joel Franck and FHC engineer Ron Franklin—creators, www.tgt.vanderbilt.edu/reu2/REU2002/chris.ppt.

Tear Away Introducer Sets (INTRADYN), B. Braun Medical, Inc. http://www.bbraunusa.com.

Truwit et al., Prospective Stereotaxy: A Novel Method of Trajectory Alignment Using Real-Time Image Guidance, J. Magn. Reson. Imag., 2001, 13:452-457.

Willems et al., Frameless Stereotaxy, VHL Family Alliance, http://www.vhl.org/newsletter/vhl2000/00aefrst.htm.

Wirtz et al., Image-Guided Neurosurgery with Intraoperative MRI: Update of Frameless Stereotaxy and Radicality Control, Sterotact Funct Neurosurg 1997, 68:39-43.

Yoda, Decoupling technique for transmit coils in NMR spectroscopy and imaging, NMR Biomed, 1990, 27-30, 3(1).

Notification of Transmittal of the International Search Report and the Written Opinion of the International Searching Authority, or the Declaration; Mailing Date: Mar. 20, 2009.

* cited by examiner

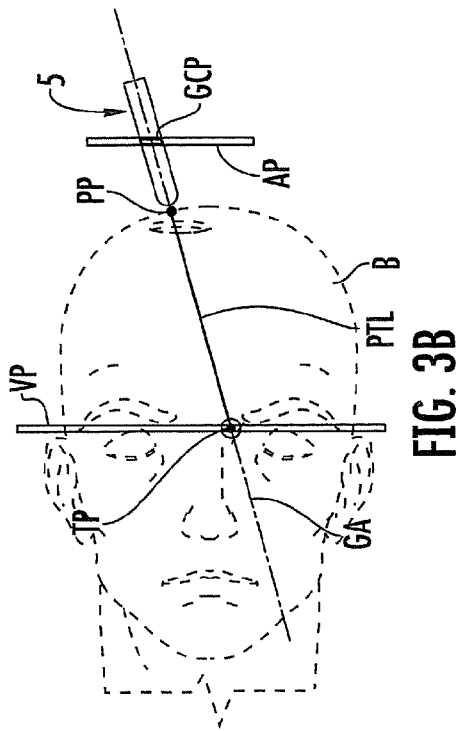
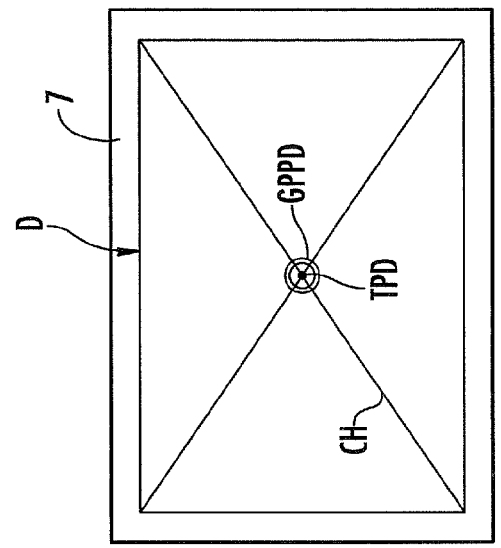
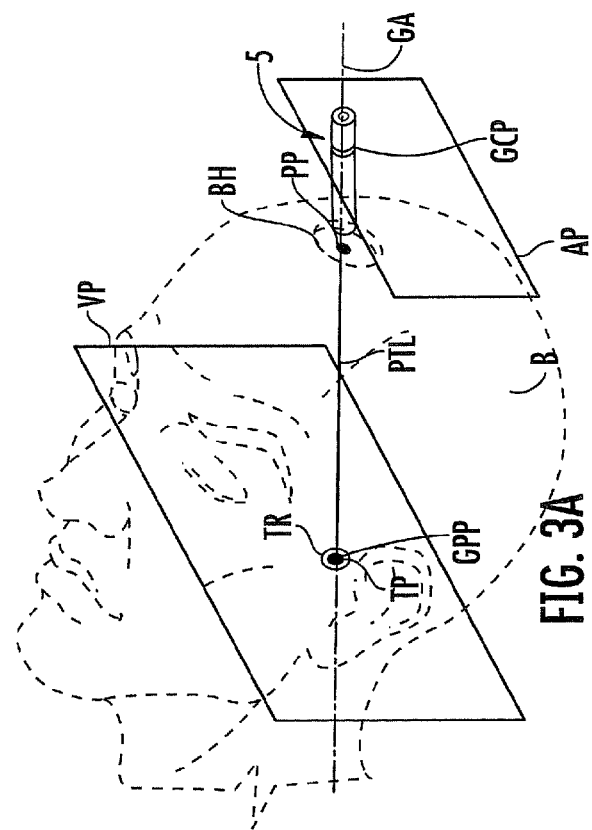
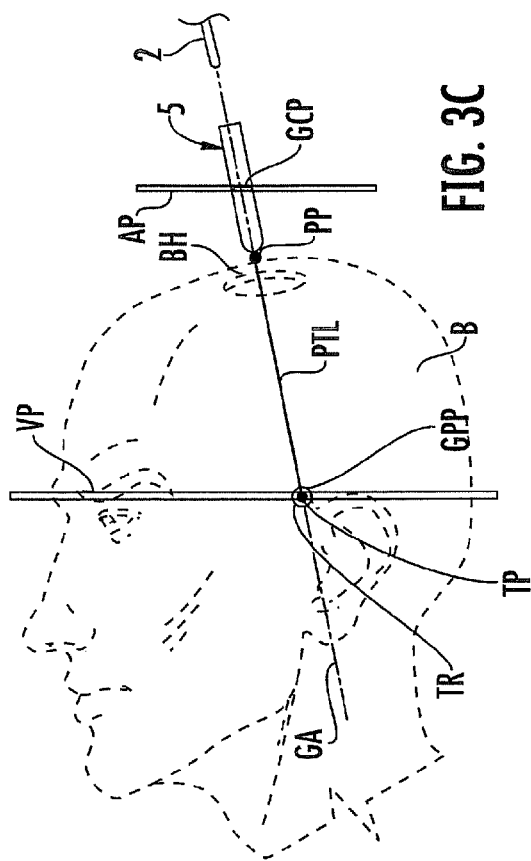
FIG. 3A
FIG. 3B
FIG. 3C
FIG. 4

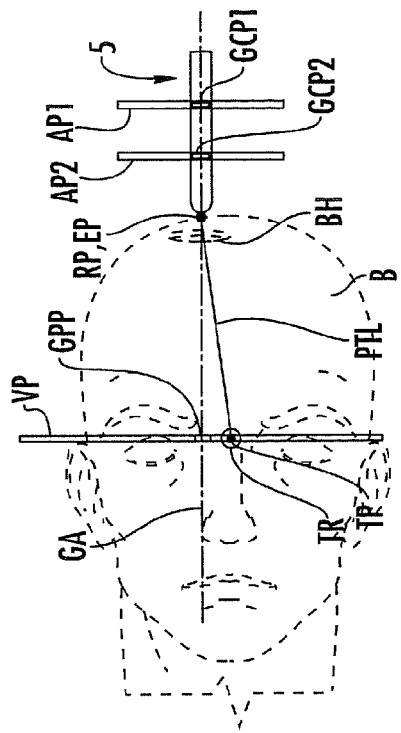
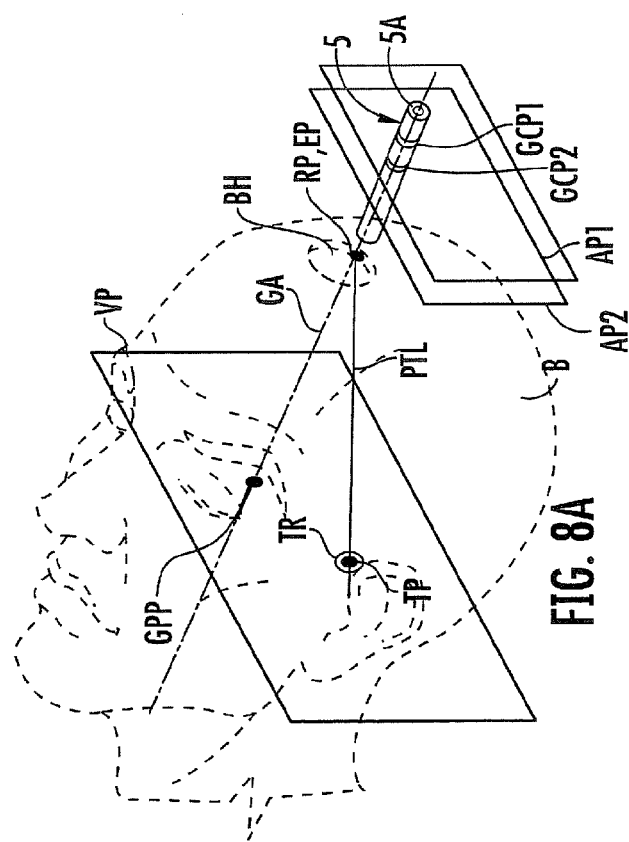
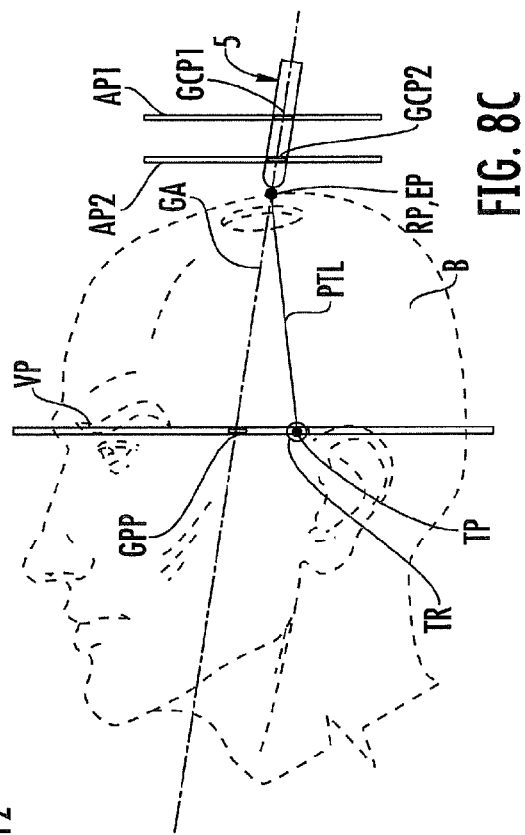
FIG. 8A
FIG. 8B
FIG. 8C

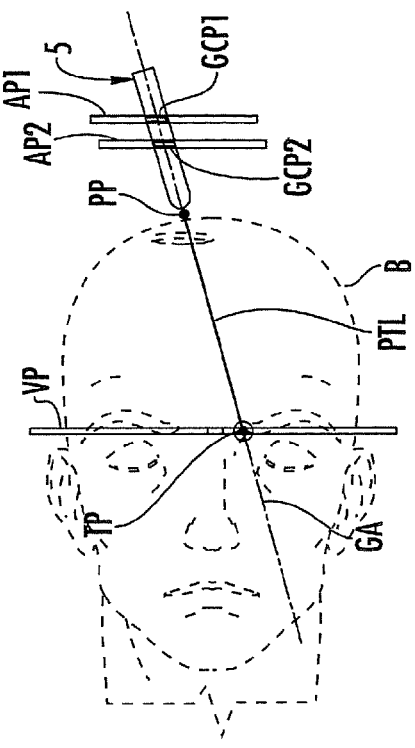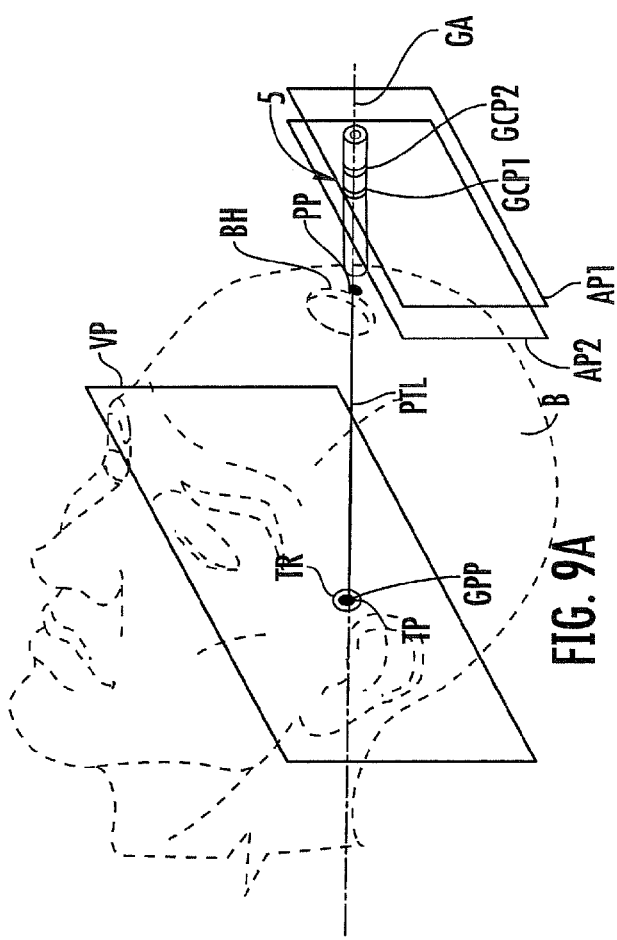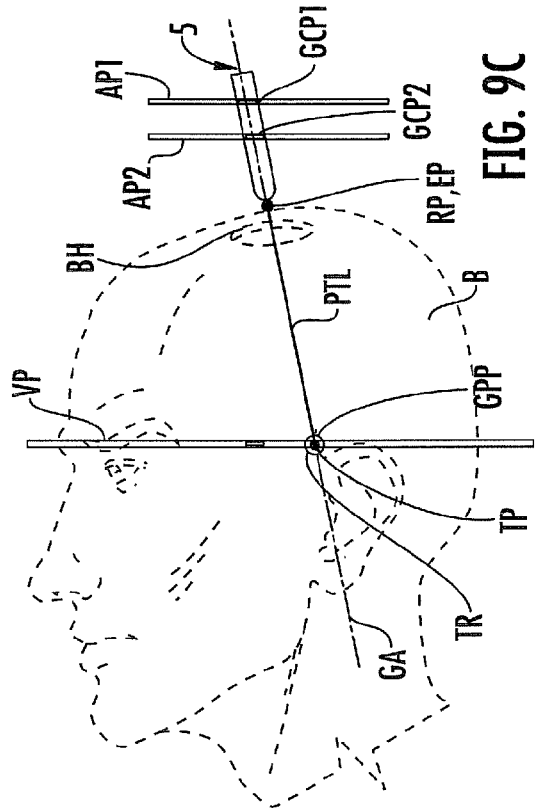

US 8,340,743 B2

METHODS, SYSTEMS AND COMPUTER PROGRAM PRODUCTS FOR POSITIONING A GUIDANCE APPARATUS RELATIVE TO A PATIENT

RELATED APPLICATION(S)

This application claims the benefit of and priority to U.S. Provisional Patent Application No. 60/989,525, filed Nov. 21, 2007, the disclosure of which is incorporated herein by reference as if set forth in its entirety.

FIELD OF THE INVENTION

The present invention relates generally to medical systems and methods and, more particularly, to medical systems and methods for intrabody procedures.

BACKGROUND OF THE INVENTION

Deep Brain Stimulation (DBS) is becoming an acceptable therapeutic modality in neurosurgical treatment of patients suffering from chronic pain, Parkinson's disease or seizure, and other medical conditions. Other electro-stimulation therapies have also been carried out or proposed using internal stimulation of the sympathetic nerve chain and/or spinal cord, etc.

One example of a prior art DBS system is the Activa® system from Medtronic, Inc. The Activa® system includes an implantable pulse generator stimulator that is positioned in the chest cavity of the patient and a lead with axially spaced apart electrodes that is implanted with the electrodes disposed in neural tissue. The lead is tunneled subsurface from the brain to the chest cavity connecting the electrodes with the pulse generator. These leads can have multiple exposed electrodes at the distal end that are connected to conductors which run along the length of the lead and connect to the pulse generator placed in the chest cavity.

It is believed that the clinical outcome of certain medical procedures, particularly those using DBS, may depend on the precise location of the electrodes that are in contact with the tissue of interest. For example, to treat Parkinson's tremor, presently the DBS probes are placed in neural tissue with the electrodes transmitting a signal to the thalamus region of the brain. DBS stimulation leads are conventionally implanted during a stereotactic surgery, based on pre-operative MRI and CT images. These procedures can be long in duration and may have reduced efficacy as it has been reported that, in about 30% of the patients implanted with these devices, the clinical efficacy of the device/procedure is less than optimum. Notwithstanding the above, there remains a need for alternative MRI-guided interventional tools for DBS, as well as for other interventional medical procedures.

SUMMARY OF EMBODIMENTS OF THE INVENTION

Some embodiments of the present invention are directed to methods for positioning a guide device for placement of an interventional object in a body, the guide device having a guide axis. The methods include: determining a target point in the body and a reference point, wherein the target point and the reference point define a planned trajectory line (PTL) extending through each; determining a visualization plane, wherein the PTL intersects the visualization plane at a sighting point; mounting the guide device relative to the body to move with respect to the PTL, wherein the guide device does not intersect the visualization plane; determining a point of intersection (GPP) between the guide axis and the visualization plane; and aligning the GPP with the sighting point in the visualization plane.

Some embodiments of the present invention are directed to methods for positioning a guide device for placement of an interventional object in a body, the guide device having a guide axis. The methods include: determining a target point in the body and a pivot point, wherein the target point and the pivot point define a planned trajectory line (PTL) extending through each; determining a visualization plane, wherein the PTL intersects the visualization plane at a sighting point, and wherein the sighting point is located on a segment of the PTL on a side of the pivot point proximate the target point; mounting the guide device relative to the body to pivot about the pivot point with respect to the PTL; determining a point of intersection (GPP) between the guide axis and the visualization plane; and aligning the GPP with the sighting point in the visualization plane.

Some embodiments of the present invention are directed to methods for positioning a guide device for placement of an interventional object in a body, the guide device having a guide axis. The methods include: determining a target point in the body and a reference point, wherein the target point and the reference point define a planned trajectory line (PTL) extending through each; determining a visualization plane, wherein the PTL intersects the visualization plane at a sighting point, and wherein the sighting point is located within the body; mounting the guide device relative to the body to move with respect to the PTL; determining a point of intersection (GPP) between the guide axis and the visualization plane; and aligning the GPP with the sighting point in the visualization plane.

Some embodiments of the present invention are directed to methods for positioning a guide device for placement of an interventional object in a body, the guide device having a guide axis. The methods include: determining a target point in the body and a reference point, wherein the target point and the reference point define a plained trajectory line (PTL) extending through each; determining a visualization plane, wherein the PTL intersects the visualization plane at a sighting point, and wherein the PTL is orthogonal to the visualization plane; mounting the guide device relative to the body to move with respect to the PTL; determining a point of intersection (GPP) between the guide axis and the visualization plane; and aligning the GPP with the sighting point in the visualization plane.

Some embodiments of the present invention are directed to methods for positioning a guide device for placement of an interventional object in a body, the guide device having a guide axis. The methods include: determining a target point in the body and a reference point, wherein the target point and the reference point define a planned trajectory line (PTL) extending through each; determining a visualization plane, wherein the PTL intersects the visualization plane at a sighting point; mounting the guide device relative to the body to translate with respect to the PTL; determining a point of intersection (GPP) between the guide axis and the visualization plane; and aligning the GPP with the sighting point in the visualization plane.

According to embodiments of the present invention, a system for positioning a guide device for placement of an interventional object in a body includes a guide device having a guide axis and a controller. The controller is configured to determine a target point in the body and a reference point, wherein the target point and the reference point define a planned trajectory line (PTL) extending through each; determine a visualization plane, wherein the PTL intersects the visualization plane at a sighting point; and determine a point of intersection (GPP) between the guide axis and the visualization plane. The guide device is mountable relative to the body to move with respect to the PTL, and such that the guide device does not intersect the visualization plane. The guide device can be adjusted with respect to the body to align the GPP with the sighting point in the visualization plane.

According to embodiments of the present invention, a system for positioning a guide device for placement of an interventional object in a body includes a guide device having a guide axis and a controller. The controller is configured to determine a target point in the body and a pivot point, wherein the target point and the pivot point define a planned trajectory line (PTL) extending through each; determine a visualization plane, wherein the PTL intersects the visualization plane at a sighting point and the sighting point is located on a side of the pivot point proximate the target point; and determine a point of intersection (GPP) between the guide axis and the visualization plane. The guide device is mountable relative to the body to pivot about the pivot point with respect to the PTL. The guide device can be adjusted with respect to the body to align the GPP with the sighting point in the visualization plane.

According to embodiments of the present invention, a system for positioning a guide device for placement of an interventional object in a body includes a guide device having a guide axis and a controller. The controller is configured to determine a target point in the body and a reference point, wherein the target point and the reference point define a planned trajectory line (PTL) extending through each; determine a visualization plane, wherein the PTL intersects the visualization plane at a sighting point and the sighting point is located within the body; and determine a point of intersection (GPP) between the guide axis and the visualization plane. The guide device is mountable relative to the body to move with respect to the PTL. The guide device can be adjusted with respect to the body to align the GPP with the sighting point in the visualization plane.

According to embodiments of the present invention, a system for positioning a guide device for placement of an interventional object in a body includes a guide device having a guide axis and a controller. The controller is configured to determine a target point in the body and a reference point, wherein the target point and the reference point define a planned trajectory line (PTL) extending through each; determine a visualization plane, wherein the PTL intersects the visualization plane at a sighting point and the PTL is orthogonal to the visualization plane; and determine a point of intersection (GPP) between the guide axis and the visualization plane. The guide device is mountable relative to the body to move with respect to the PTL. The guide device can be adjusted with respect to the body to align the GPP with the sighting point in the visualization plane.

According to embodiments of the present invention, a system for positioning a guide device for placement of an interventional object in a body includes a guide device having a guide axis and a controller. The controller is configured to determine a target point in the body and a reference point, wherein the target point and the reference point define a planned trajectory line (PTL) extending through each; determine a visualization plane, wherein the PTL intersects the visualization plane at a sighting point; and determine a point of intersection (GPP) between the guide axis and the visualization plane. The guide device is mountable relative to the body to translate with respect to the PTL. The guide device can be adjusted with respect to the body to align the GPP with the sighting point in the visualization plane.

According to embodiments of the present invention, a computer program product for positioning a guide device for placement of an interventional object in a body, the guide device having a guide axis, includes a computer readable medium having computer readable program code embodied therein. The computer usable program code includes: computer readable program code configured to determine a target point in the body and a reference point, wherein the target point and the reference point define a planned trajectory line (PTL) extending through each; computer readable program code configured to determine a visualization plane, wherein the PTL intersects the visualization plane at a sighting point; and computer readable program code configured to determine a point of intersection (GPP) between the guide axis and the visualization plane when the guide device does not intersect the visualization plane.

According to embodiments of the present invention, a computer program product for positioning a guide device for placement of an interventional object in a body, the guide device having a guide axis, includes a computer readable medium having computer readable program code embodied therein. The computer usable program code includes: computer readable program code configured to determine a target point in the body and a pivot point, wherein the target point and the pivot point define a planned trajectory line (PTL) extending through each, and wherein the sighting point is located on a segment of the PTL on a side of the pivot point proximate the target point; computer readable program code configured to determine a visualization plane, wherein the PTL intersects the visualization plane at a sighting point; and computer readable program code configured to determine a point of intersection (GPP) between the guide axis.

According to embodiments of the present invention, a computer program product for positioning a guide device for placement of an interventional object in a body, the guide device having a guide axis, includes a computer readable medium having computer readable program code embodied therein. The computer usable program code includes: computer readable program code configured to determine a target point in the body and a reference point, wherein the target point and the reference point define a planned trajectory line (PTL) extending through each; computer readable program code configured to determine a visualization plane, wherein the PTL intersects the visualization plane at a sighting point and the sighting point is located within the body; and computer readable program code configured to determine a point of intersection (GPP) between the guide axis.

According to embodiments of the present invention, a computer program product for positioning a guide device for placement of an interventional object in a body, the guide device having a guide axis, includes a computer readable medium having computer readable program code embodied therein. The computer usable program code includes: computer readable program code configured to determine a target point in the body and a reference point, wherein the target point and the reference point define a planned trajectory line (PTL) extending through each; computer readable program code configured to determine a visualization plane, wherein the PTL intersects the visualization plane at a sighting point, and wherein the PTL is orthogonal to the visualization plane; and computer readable program code configured to determine a point of intersection (GPP) between the guide axis.

Further features, advantages and details of the present invention will be appreciated by those of ordinary skill in the art from a reading of the figures and the detailed description of the preferred embodiments that follow, such description being merely illustrative of the present invention.

BRIEF DESCRIPTION OF THE DRAWINGS

FIGS. 3A, 3B and 3C are schematic perspective, top and side views of the patient body and logical elements of FIGS. 1A-1C but showing the guide device is oriented in a second, aligned position.

FIG. 4 is a schematic view of an image displayed to an operator when the guide device is in the second position.

FIGS. 8A, 8B and 8C are schematic perspective, top and side views of a portion of a patient body and logical elements associated with methods and systems according to further embodiments of the present invention wherein a guide device thereof is oriented in a first, non-aligned position.

FIGS. 9A, 9B and 9C are schematic perspective, top and side views of the portion of the patient body and logical elements of FIGS. 8A-8C but showing the guide device is oriented in a second, aligned position.

DETAILED DESCRIPTION OF EMBODIMENTS OF THE INVENTION

Figure 1B:
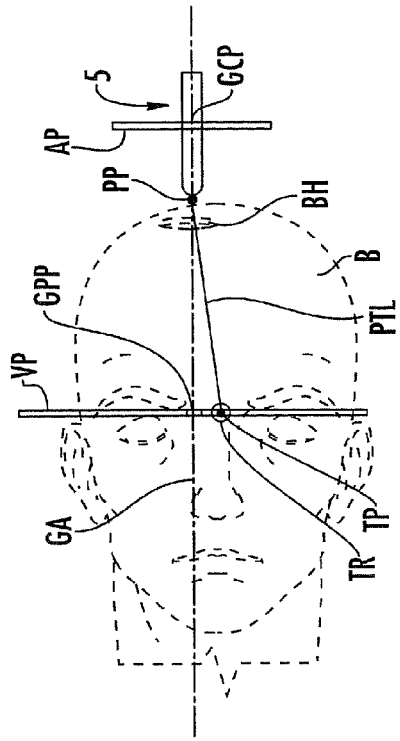
FIGS. 1A, 1B, and 1C are schematic perspective, top and side views of a portion of patient body and logical elements associated with methods and systems according to embodiments of the present invention wherein a guide device thereof is oriented in a first, non-aligned position.

The present invention now is described more fully hereinafter with reference to the accompanying drawings, in which some embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under". The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Exemplary embodiments are described below with reference to block diagrams and/or flowchart illustrations of methods, apparatus (systems and/or devices) and/or computer program products. It is understood that a block of the block diagrams and/or flowchart illustrations, and combinations of blocks in the block diagrams and/or flowchart illustrations, can be implemented by computer program instructions. These computer program instructions may be provided to a processor of a general purpose computer, special purpose computer, and/or other programmable data processing apparatus to produce a machine, such that the instructions, which execute via the processor of the computer and/or other programmable data processing apparatus, create means (functionality) and/or structure for implementing the functions/acts specified in the block diagrams and/or flowchart block or blocks.

These computer program instructions may also be stored in a computer-readable memory that can direct a computer or other programmable data processing apparatus to function in a particular manner, such that the instructions stored in the computer-readable memory produce an article of manufacture including instructions which implement the functions/acts specified in the block diagrams and/or flowchart block or blocks.

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions/acts specified in the block diagrams and/or flowchart block or blocks.

Accordingly, exemplary embodiments may be implemented in hardware and/or in software (including firmware, resident software, micro-code, etc.). Furthermore, exemplary embodiments may take the form of a computer program product on a computer-usable or computer-readable storage medium having computer-usable or computer-readable program code embodied in the medium for use by or in connection with an instruction execution system. In the context of this document, a computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Computer program code for carrying out operations of data processing systems discussed herein may be written in a high-level programming language, such as Java, AJAX (Asynchronous JavaScript), C, and/or C++, for development convenience. In addition, computer program code for carrying out operations of exemplary embodiments may also be written in other programming languages, such as, but not limited to, interpreted languages. Some modules or routines may be written in assembly language or even micro-code to enhance performance and/or memory usage. However, embodiments are not limited to a particular programming language. It will be further appreciated that the functionality of any or all of the program modules may also be implemented using discrete hardware components, one or more application specific integrated circuits (ASICs), or a programmed digital signal processor or microcontroller.

The flowcharts and block diagrams of certain of the figures herein illustrate exemplary architecture, functionality, and operation of possible implementations of embodiments of the present invention. In this regard, each block in the flow charts or block diagrams represents a module, segment, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently.

The term "MRI-visible" means that a device or feature thereof is visible, directly or indirectly, in an MRI image. The visibility may be indicated by the increased SNR of the MRI signal proximate to the device (the device can act as an MRI receive antenna to collect signal from local tissue) and/or that the device actually generates MRI signal itself, such as via suitable hydro-based coatings and/or fluid (typically aqueous solutions) filled cavities.

The term "MRI-compatible" means that a device is safe for use in an MRI environment and/or can operate as intended in an MRI environment, and, as such, if residing within the high-field strength region of the magnetic field, is typically made of a non-ferromagnetic MRI-compatible material(s) suitable to reside and/or operate in a high magnetic field environment.

The term "programmatically" refers to operations directed and/or primarily carried out electronically by computer program modules, code and instructions.

The term "fiducial marker" refers to a marker that can be identified visually and/or using electronic image recognition, electronic interrogation of MRI image data, or three-dimensional electrical signals to define a position or orientation and/or find a feature or component in 3-D space.

According to embodiments of the present invention, methods, systems and computer program products are provided for positioning a guidance apparatus relative to a patient. In some embodiments, the methods, systems and computer program products form a part of or operate with MRI-compatible interventional systems. In some embodiments, the systems include trajectory guide systems and/or apparatus and related components and methods. According to some embodiments, the trajectory guide apparatus and methods are frameless stereotactic trajectory guide apparatus that may be particularly suitable for deep brain interventional procedures, but may be used in other target anatomical locations as well. In some embodiments, the guide apparatus is used to place implantable DBS leads for brain stimulation, typically deep brain stimulation.

Some embodiments of the invention are directed to MRI interventional procedures and provide interventional tools and/or therapies that may be used to locally place surgical interventional objects, tools or therapies in vivo to site specific regions using an MRI system. The interventional tools can be used to define an MRI-guided trajectory or access path to an in vivo treatment site.

In some embodiments, an MRI can be used to visualize (and/or locate) a therapeutic region of interest inside the brain and utilize an MRI to visualize (and/or locate) an interventional tool or tools that will be used to deliver therapy and/or to place a chronically implanted device that will deliver one or more therapies. Then, using the imaging data produced by the MRI system regarding the location of the therapeutic region of interest and the location of the interventional tool, the system and/or physician can make positional adjustments to the interventional tool so as to align the trajectory of the interventional tool, so that when inserted into the body, the trajectory of the interventional tool will intersect with the therapeutic region of interest. With the interventional tool now aligned with the therapeutic region of interest, an interventional probe can be advanced, such as through an open lumen inside of the interventional tool, so that the interventional probe follows the trajectory of the interventional tool and proceeds to the therapeutic region of interest. The interventional tool and the interventional probe may or may not be part of the same component or structure.

Methods according to embodiments of the present invention will now be described with reference to the flow charts of FIGS. 11-15.

Figure 11:
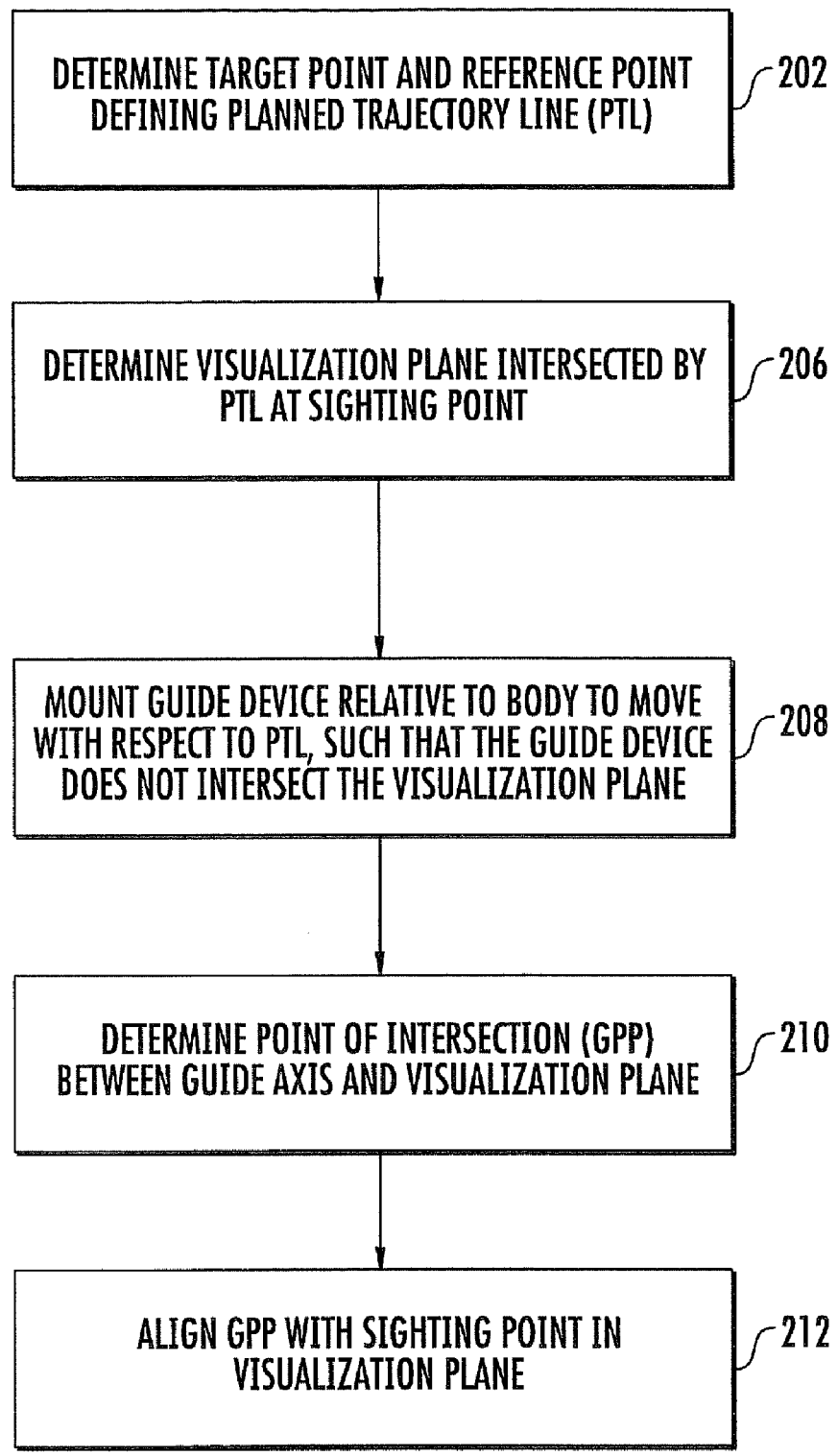
FIGS. 11-15 are flow charts illustrating methods and/or operations according to embodiments of the present invention.

With reference to FIG. 11, a method for positioning a guide device for placement of an interventional object in a body includes determining a target point in the body and a reference point (Block 202). The target point and the reference point define a planned trajectory line (PTL) that extends through each. A visualization plane is determined (Block 206). The PTL intersects the visualization plane at a sighting point. The guide device is mounted relative to the body to move with respect to the PTL (Block 208). The guide device does not intersect the visualization plane. A point of intersection (GPP) between the guide axis and the visualization plane is determined (Block 210). The GPP is aligned with the sighting point in the visualization plane (Block 212).

Figure 12:
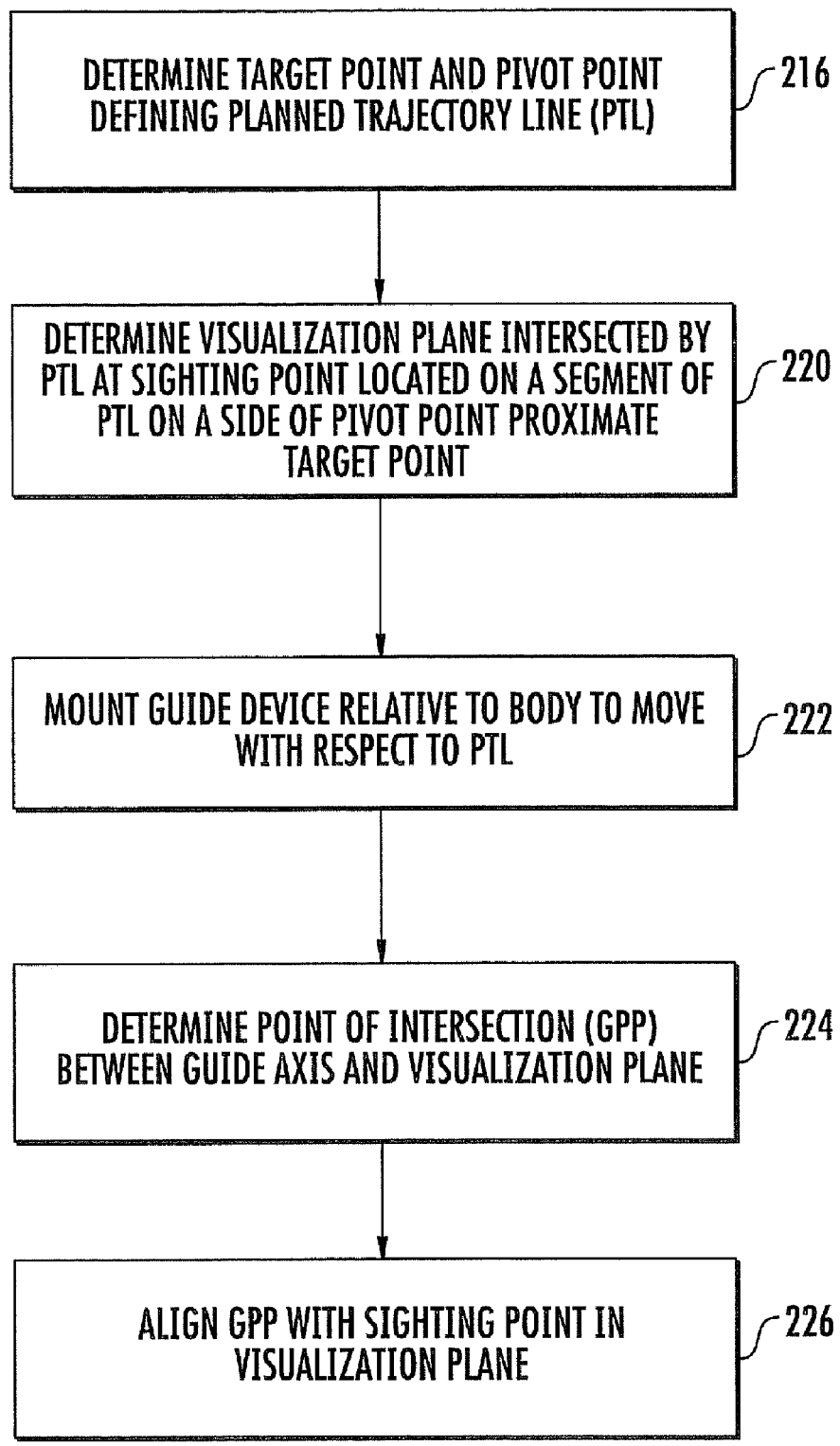

With reference to FIG. 12, a method for positioning a guide device for placement of an interventional object in a body includes determining a target point in the body and a pivot point (Block 216). The pivot point and the reference point define a planned trajectory line (PTL) that extends through each. A visualization plane is determined (Block 220). The PTL intersects the visualization plane at a sighting point and the sighting point is located on a segment of the PTL on a side of the pivot point proximate the target point. The guide device is mounted relative to the body to be able to move with respect to the PTL (Block 222). A point of intersection (GPP) between the guide axis and the visualization plane is determined (Block 224). The GPP is aligned with the sighting point in the visualization plane (Block 226).

Figure 13:
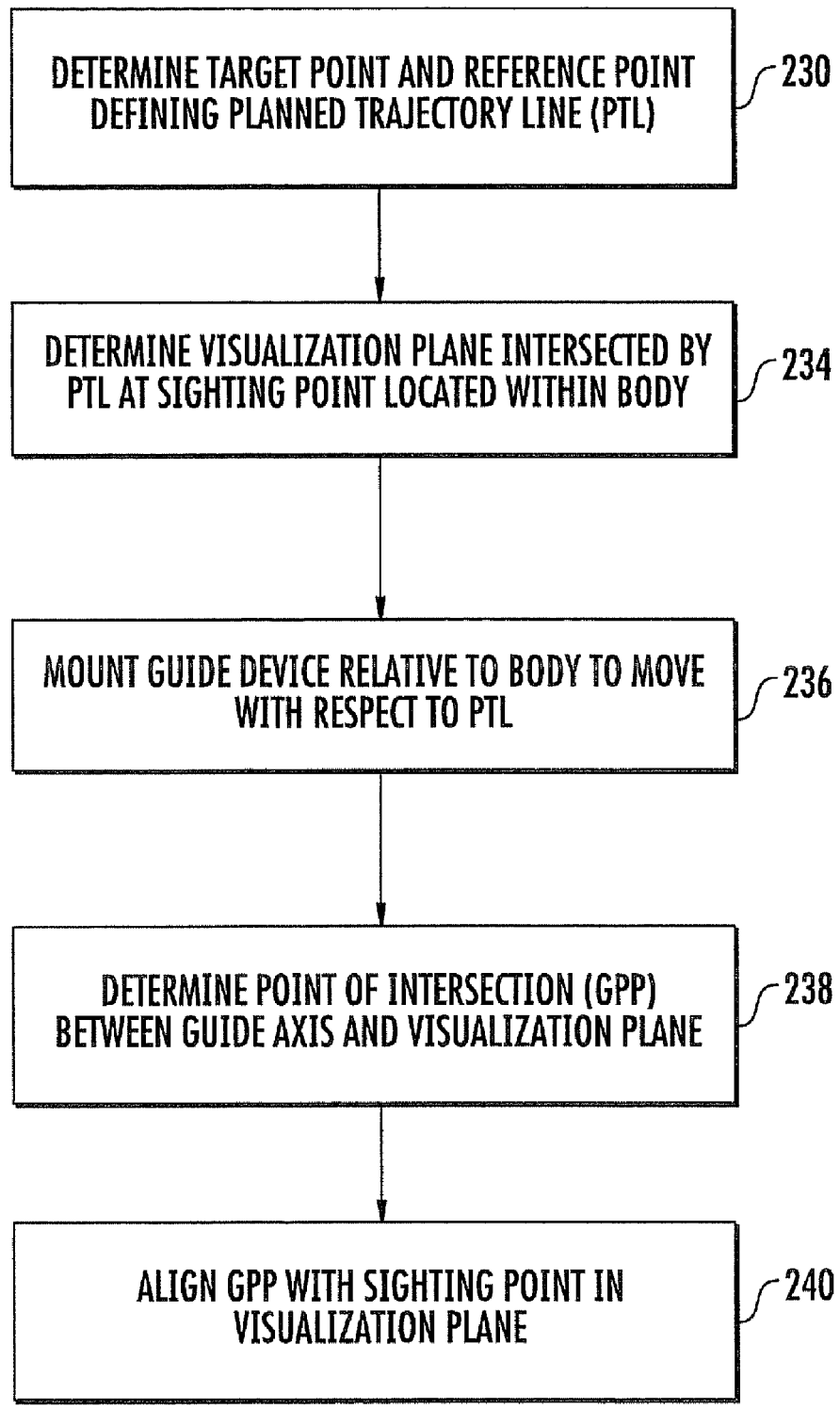

With reference to FIG. 13, a method for positioning a guide device for placement of an interventional object in a body includes determining a target point in the body and a reference point (Block 230). The target point and the reference point define a planned trajectory line (PTL) extending through each. A visualization plane is determined (Block 234). The PTL intersects the visualization plane at a sighting point and the sighting point is located within the body. The guide device is mounted relative to the body to move with respect to the PTL (Block 236). A point of intersection (GPP) between the guide axis and the visualization plane is determined (Block 238). The GPP is aligned with the sighting point in the visualization plane (Block 240).

Figure 14:
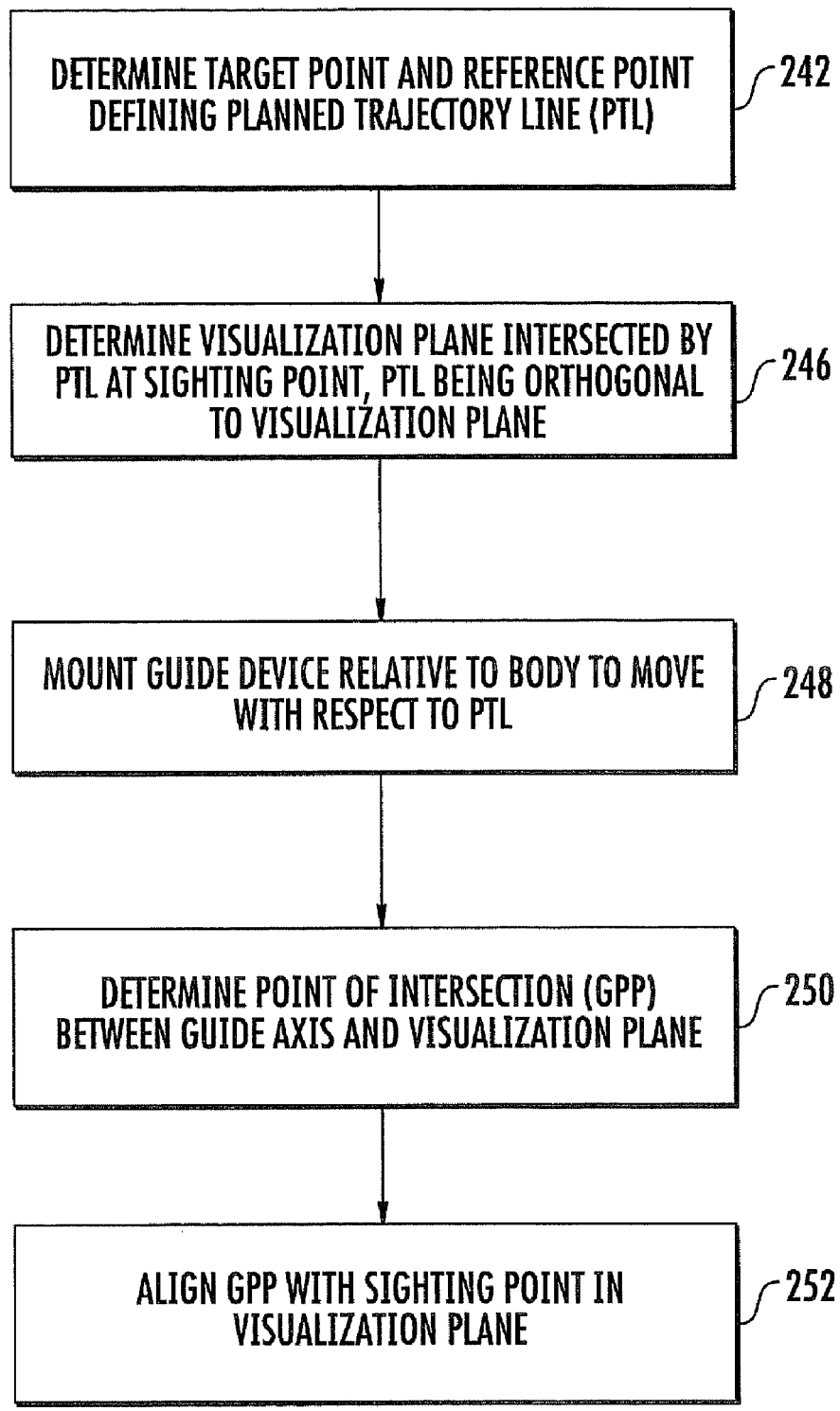

With reference to FIG. 14, a method for positioning a guide device for placement of an interventional object in a body includes determining a target point in the body and a reference point (Block 242). The target point and the reference point define a planned trajectory line (PTL) extending through each. A visualization plane is determined (Block 246). The PTL intersects the visualization plane at a sighting point and the PTL is orthogonal to the visualization plane. The guide device is mounted relative to the body to move with respect to the PTL (Block 248). A point of intersection (GPP) between the guide axis and the visualization plane is determined (Block 250). The GPP is aligned with the sighting point in the visualization plane (Block 252).

Figure 15:
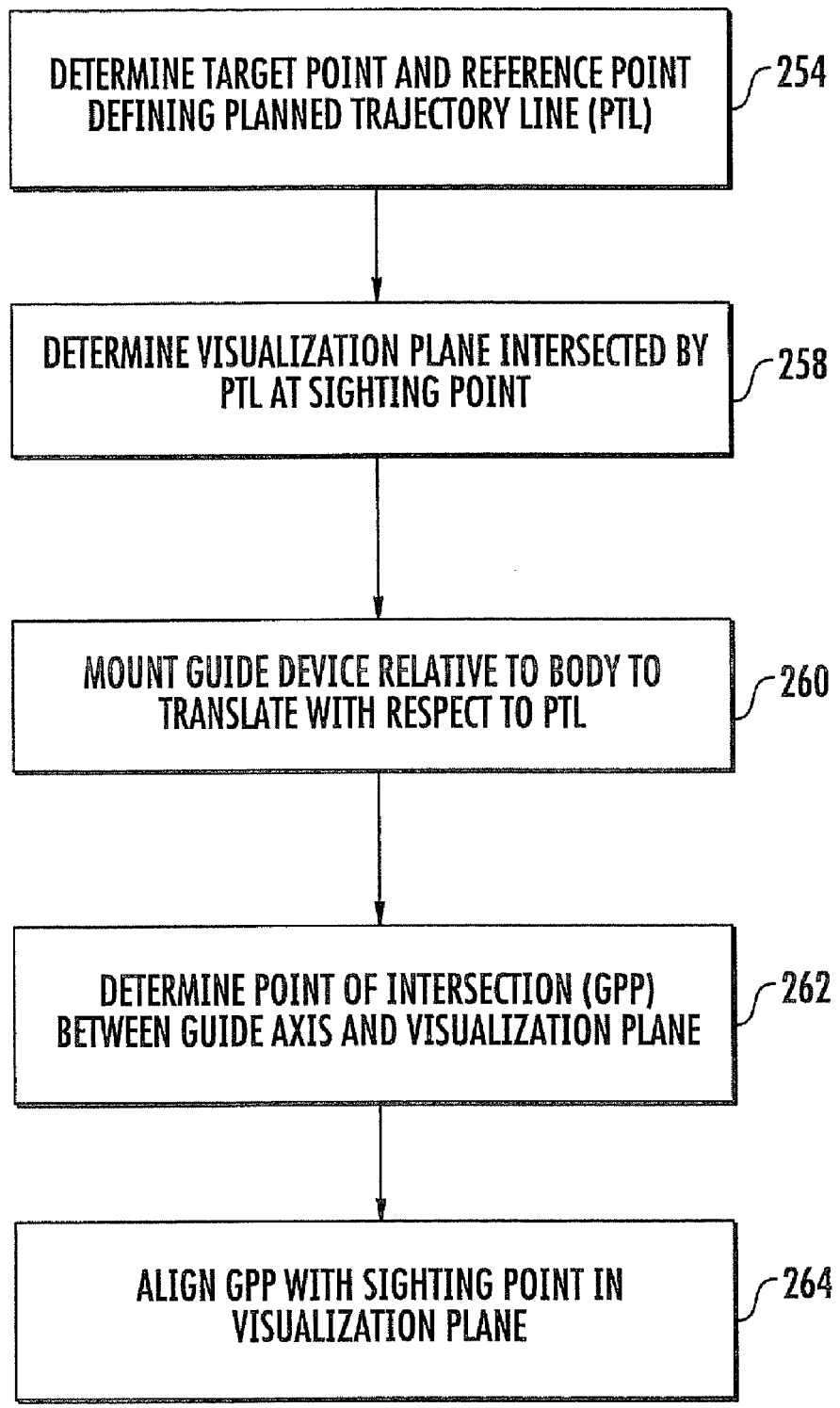

With reference to FIG. 15, a method for positioning a guide device for placement of an interventional object in a body includes determining a target point in the body and a reference point (Block 254). The target point and the reference point define a planned trajectory line (PTL) extending through each. A visualization plane is determined (Block 258). The PTL intersects the visualization plane at a sighting point. The guide device is mounted relative to the body to translate with respect to the PTL (Block 260). A point of intersection (GPP) between the guide axis and the visualization plane is determined (Block 262). The GPP is aligned with the sighting point in the visualization plane (Block 264).

Systems and methods according to embodiments of the present invention will be described with reference to FIGS. 1A-4. These exemplary operations are described with respect to deep brain interventional procedures. While embodiments of the present invention are particularly suitable for same, embodiments of the present invention are not limited to use with deep brain procedures, however, and may be suitable for other surgical uses including robotic or other types of intrabody surgeries for other locations.

Methods and systems according to embodiments of the present invention are described hereinbelow as using or incorporating MRI scanning or scanners. However, some embodiments may instead or additionally employ other scanning modalities including CT, ultrasound and/or suitable non-scanning apparatus.

The order of at least certain of the steps described below may be rearranged and some of the steps and apparatus described below may be omitted or modified in accordance with further embodiments of the present invention.

Figure 1A:
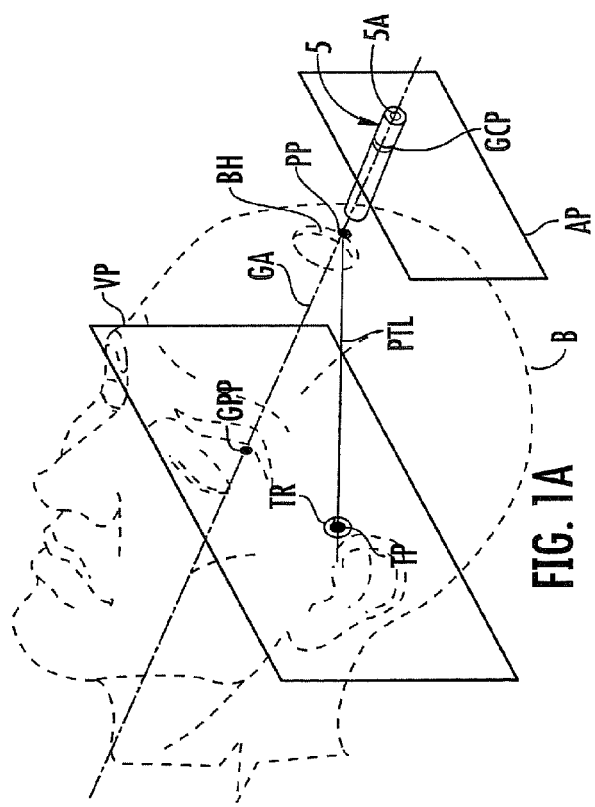
Figure 1C:
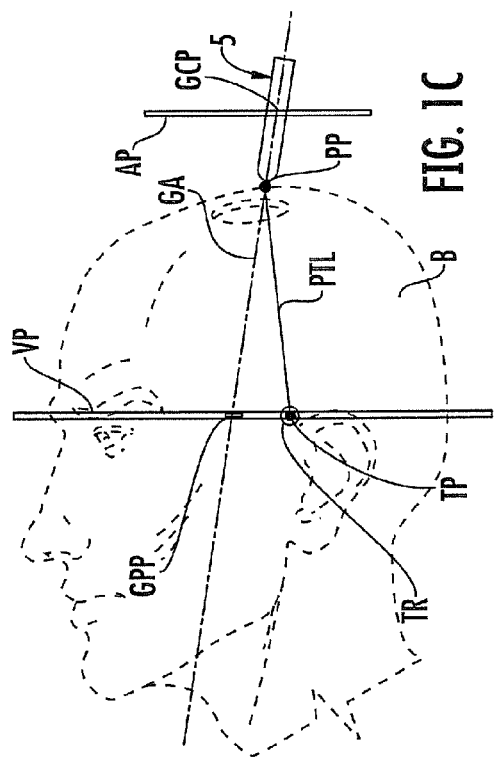

A body B of a patient (as shown, a patient's head) is shown schematically in FIGS. 1A-C. FIG. 1A is a perspective view, FIG. 1B is a top view, and FIG. 1C is a side view.

The body B of the patient is scanned using an MRI scanner. The MRI scanner scans the body B and generates corresponding MR image data. From the MR image data, MR images are obtained of the patient's body. According to some embodiments, the scans include scans of the patient's head and the MR images obtained visualize the patient's skull and brain.

In accordance with embodiments of the present invention, a target region TR (which may also be referred to as a target therapeutic site or region of interest) in the body B is identified. For example, the target region TR may be identified by MRI scanning the body B and with reference to known physiological landmarks. For example, reference may be made to physiological landmarks such as the AC, PC and MCP points (brain atlases can give the location of different anatomies in the brain with respect to these points) and other anatomical landmarks of the patient's head.

A target point TP within the target region TR is selected and designated in a logical space in the MR image. A planned trajectory line PTL is selected and designated extending from the target point TP to a pivot point PP. The planned trajectory line PTL extends through an entry surface of the body B at a desired entry location point in the logical space. According to some embodiments, the pivot point PP is located at or proximate the entry location point. Accordingly, the target point TP and the pivot point PP define a planned trajectory line PTL, which extends through each of the target point TP and the pivot point PP. Images may be obtained in the planned plane of trajectory to confirm that the trajectory is viable (i.e., that no complications with anatomically sensitive areas should occur). The steps of identifying the target region TR, identifying the target point TP, and/or selecting and designating the planned trajectory line PTL may be executed using or with the aid of a trajectory guide module 40A as described below, for example.

A visualization plane VP is determined that intersects (and is non-parallel to) the planned trajectory line PTL at a sighting point. According to some embodiments, the visualization plane VP extends through the body B as shown. According to some embodiments and as shown, the visualization plane VP intersects the planned trajectory line PTL in the body B.

According to some embodiments and as illustrated and described hereinafter, the visualization plane VP includes the target point TP (i.e., the target point is the sighting point). However, it is contemplated that, according to further embodiments, the visualization plane VP may instead intersect the planned trajectory line PTL at a point on a segment of the planned trajectory line PTL between the target point TP and the pivot point PP or, alternatively, at a location on a segment of the planned trajectory line PTL beyond the target point TP opposite the pivot point PP so that the sighting point is offset from the target point TP. According to some embodiments, the planned trajectory line PTL is substantially orthogonal to the visualization plane VP. According to some embodiments, the visualization plane VP is an axial plane with respect to the body B.

At least one scan (e.g., an MRI scan) is then obtained along the visualization plane VP to acquire a visualization image of the body B.

A hole BH is formed in the body B to serve as an access portal to the body. For example, the hole BH may be a burr hole through the patient's skull to provide access to the brain. Alternatively, a natural lumen may serve as the access portal.

A suitable trajectory guide device 5 is mounted on or adjacent the body B proximate the burr hole BH. The trajectory guide device 5 may allow the operator to align an access path trajectory to the internal target site TP, such that the interventional/surgical device/lead, therapy, etc. will be delivered to the target site following the desired trajectory (e.g., the planned trajectory line PTL) through the cranial tissue.

According to some embodiments, the guide device 5 does not intersect the visualization plane VP. The orientation of the guide device 5 relative to the body B is adjustable. More particularly, the guide device 5 defines a guide axis GA and is adjustable such that the guide axis GA pivots about the pivot point PP. The guide axis GA can therefore be defined by the pivot point PP and any other point on the guide axis GA, including points on the guide device 5 on the guide axis GA. The guide axis GA may be defined by or aligned with a lumen 5A through which interventional instrumentation can be inserted.

The guide device 5 may initially be positioned as shown in FIGS. 1A-C such that the guide axis GA diverges from the planned trajectory line PTL and does not intersect or approach the target point TP. It may therefore be necessary or desirable to reposition the orientation of the guide device 5 with respect to the body to align the guide axis GA with the planned trajectory line PTL. In accordance with the present invention, instrumentation may be provided to enable an operator (e.g., a physician) to adjust and track the orientation of the guide axis GA relative to the planned trajectory line PTL. According to some embodiments, the operator may be able to adjust and visually track the guide axis GA in substantially real-time while the body and guide device 5 are located in an MRI scanner.

An acquisition plane AP is selected and a scan or scans (e.g., MRI scans) are obtained along the acquisition plane AP. According to some embodiments, such scans are repeatedly and substantially continuously obtained throughout the alignment procedure described hereinafter. For example, scans may be acquired at a rate of at least about seven frames per second for portions or all of the alignment procedure. The acquisition plane AP is selected such that it intersects a trackable component or portion of the guide device 5, and the position of the guide axis GA in the acquisition plane AP can be determined from the acquired image. According to some embodiments, the scan is an MRI scan and at least the trackable component or portion of the guide device 5 is MRI visible. According to some embodiments, the acquisition plane AP is selected such that it intersects the trackable component or portion of the guide device 5 throughout a selected range of adjustment motion of the guide device 5 (according to some embodiments, the entire range of adjustment). The point of intersection GCP between the acquisition plane AP and the guide axis GA of the guide device 5 (hereinafter, the "guide component point") may vary depending on the orientation of the guide device 5 and as the guide device 5 is adjusted because the travel path of the guide device 5 about the pivot point PP will be arcuate.

Using the information from the scan(s) of the acquisition plane AP, the orientation of the guide axis GA is programmatically determined by a controller. More particularly, the controller can determine the orientation of the guide axis GA from the known positions of the pivot point PP and the guide component point GCP. The controller extrapolates the guide axis GA and determines the location of the guide axis' GA intersection with the visualization plane VP. The point of intersection between the guide axis GA and the visualization plane VP is referred to herein as the guide axis projected point GPP. According to some embodiments, the point of intersection between the guide axis GA and the visualization plane VP is not a point on the guide device 5. The controller may determine or derive the location of the guide axis projected point GPP by mathematical calculation and/or any other suitable method.

Figure 2:
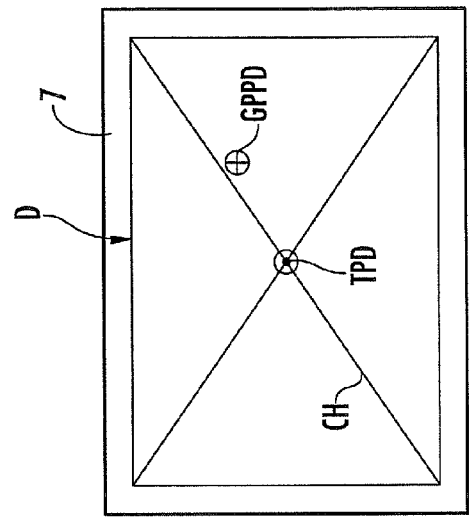
FIG. 2 is a schematic view of an exemplary image displayed to an operator when the guide device is in the first position.

The controller provides a displayed image D (e.g., on a suitable display screen device 7, typically a clinician work station) to the operator as shown in FIG. 2. FIG. 2 shows the displayed image D when the guide device 5 is positioned as shown in FIGS. 1A-C. The displayed image D includes the scan image of the visualization plane VP, which includes an image of the target region TR. The displayed image D may also include a graphic representation such as crosshairs CH with an intersection point TPD that visually indicates the location of the target point TP in the visualization plane VP. The displayed image D further includes a graphical representation GPPD of the guide axis projected point GPP. Supplemental or alternative visual representations of the guide axis projected point GPP and the target point TP may be provided, such as graphic elements (e.g., symbols such as dots) of different colors and/or shapes.

As the operator moves the guide device 5 to reorient the guide axis GA, the controller tracks the guide device 5 via the scans along the acquisition plane AP and updates the position of the graphical representation GPPD in the displayed image D. According to some embodiments, the controller updates the position of the graphical representation GPPD in the displayed image D automatically and in substantially real time. The operator can thereby use the displayed image D to track the movement of the guide axis GA relative to the planned trajectory line PTL.

The operator can move the guide device 5 until the graphical representation GPPD is on or sufficiently proximate the intersection point TPD. At this point, the guide axis GA and the planned trajectory line PTL will typically be near or substantially in alignment (i.e., coextensive). FIGS. 3A-C are views corresponding to the views of FIGS. 1A-C, respectively, wherein the guide device 5 is aligned with the planned trajectory line PTL. FIG. 4 shows the displayed image D when the guide device 5 is positioned as shown in FIGS. 3A-C.

According to some embodiments, the X, Y position of the guide device 5, and thus the guide axis GA, can be readjusted using an X-Y adjustment mechanism (for example, as discussed hereinbelow).

While in the foregoing description the guide device 5 can be tracked using MRI scans taken along the acquisition plane AP, according to some embodiments, the guide device 5 is alternatively or additionally tracked using a different tracking device or devices such as LEDs, microcoils, hydrogel coatings or markers, or other suitable devices.

Once the guide device 5 has been suitably positioned to align the guide axis GA with the planned trajectory line PTL, a scan may be acquired in a plane or planes parallel to the planned trajectory line PTL to additionally confirm that the guide device 5 and guide axis GA are properly aligned to the planned trajectory line PTL.

Once the guide device 5 is desirably positioned, an interventional device 2 (FIG. 3C) (e.g., probe, lead or the like) can be advanced through the lumen 5A of the guide device 5, into the body B and to or proximate the target point TP.

Figure 5:
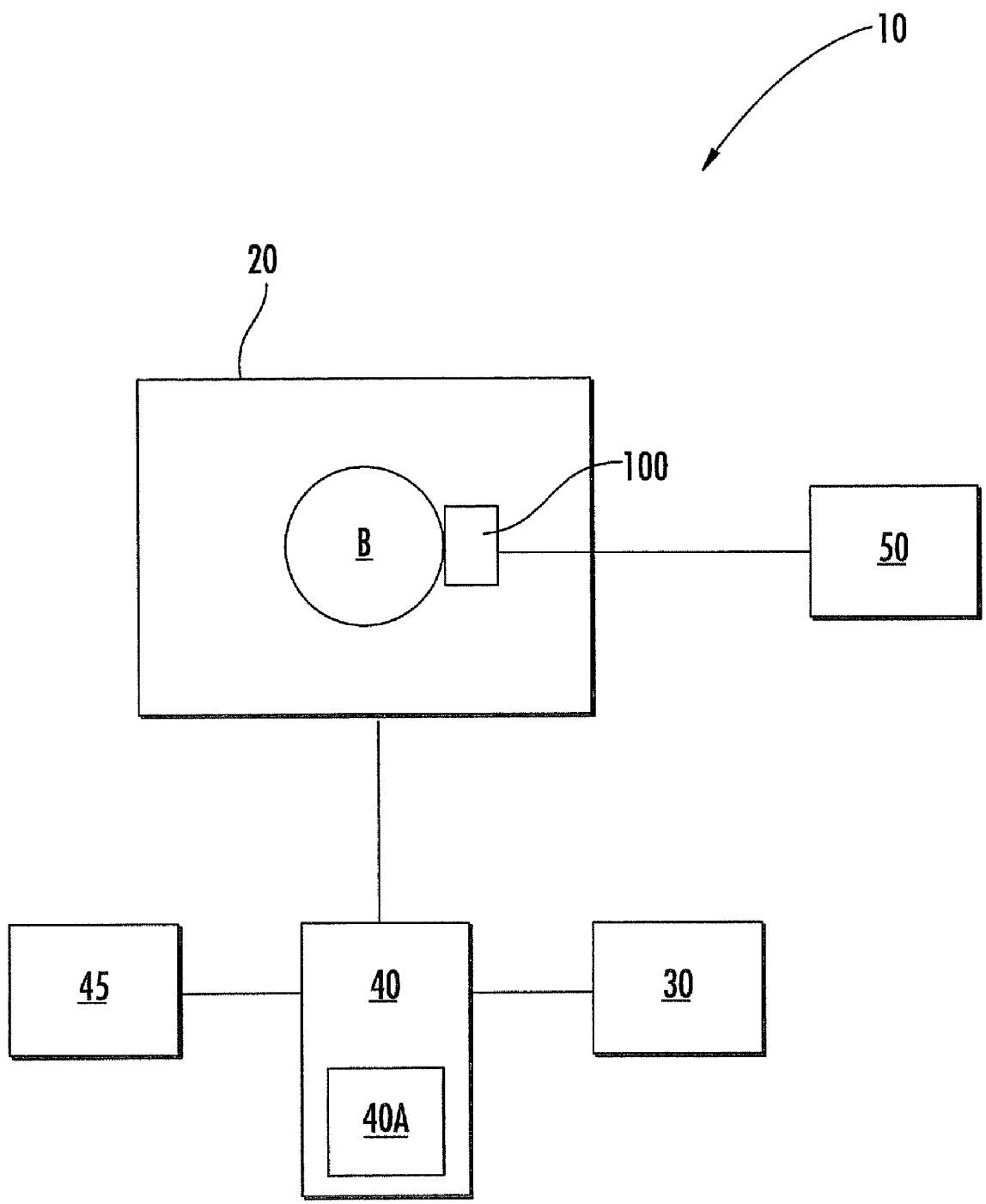
FIG. 5 is a schematic diagram of a system according to embodiments of the present invention.

With reference to FIG. 5, an exemplary interventional or trajectory guide system 10 for executing the methods discussed above is shown therein. As shown, the system 10 includes a trajectory guide apparatus 100, a scanning apparatus 20, a display 30, a controller 40, a user interface 45 and a device controller 50. The controller 40 includes, communicates with, and/or is associated with a trajectory guide module 40A.

Figure 6A:
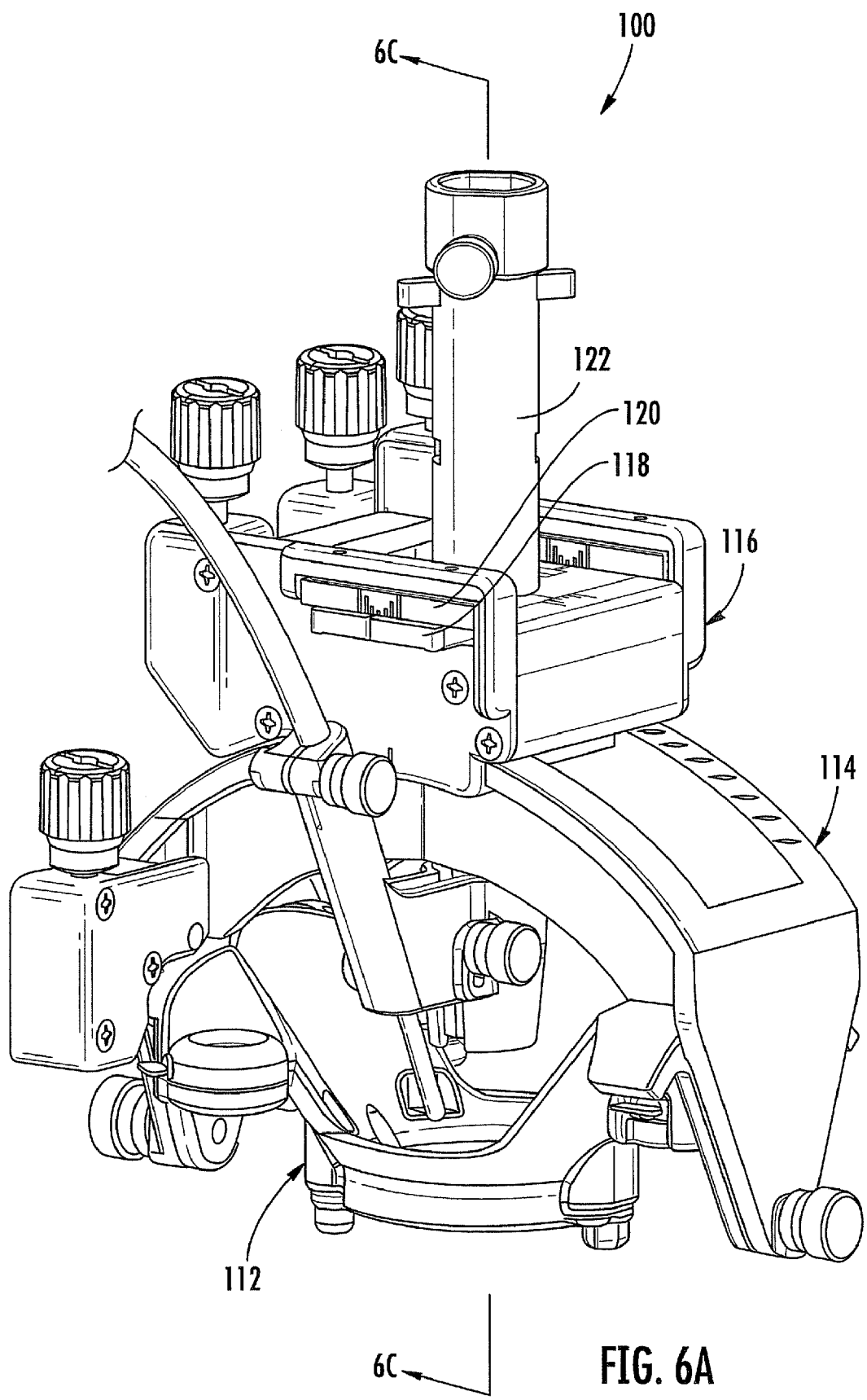
FIG. 6A is a front perspective view of a trajectory guide apparatus that may form a part of the system of FIG. 5.
Figure 6B:
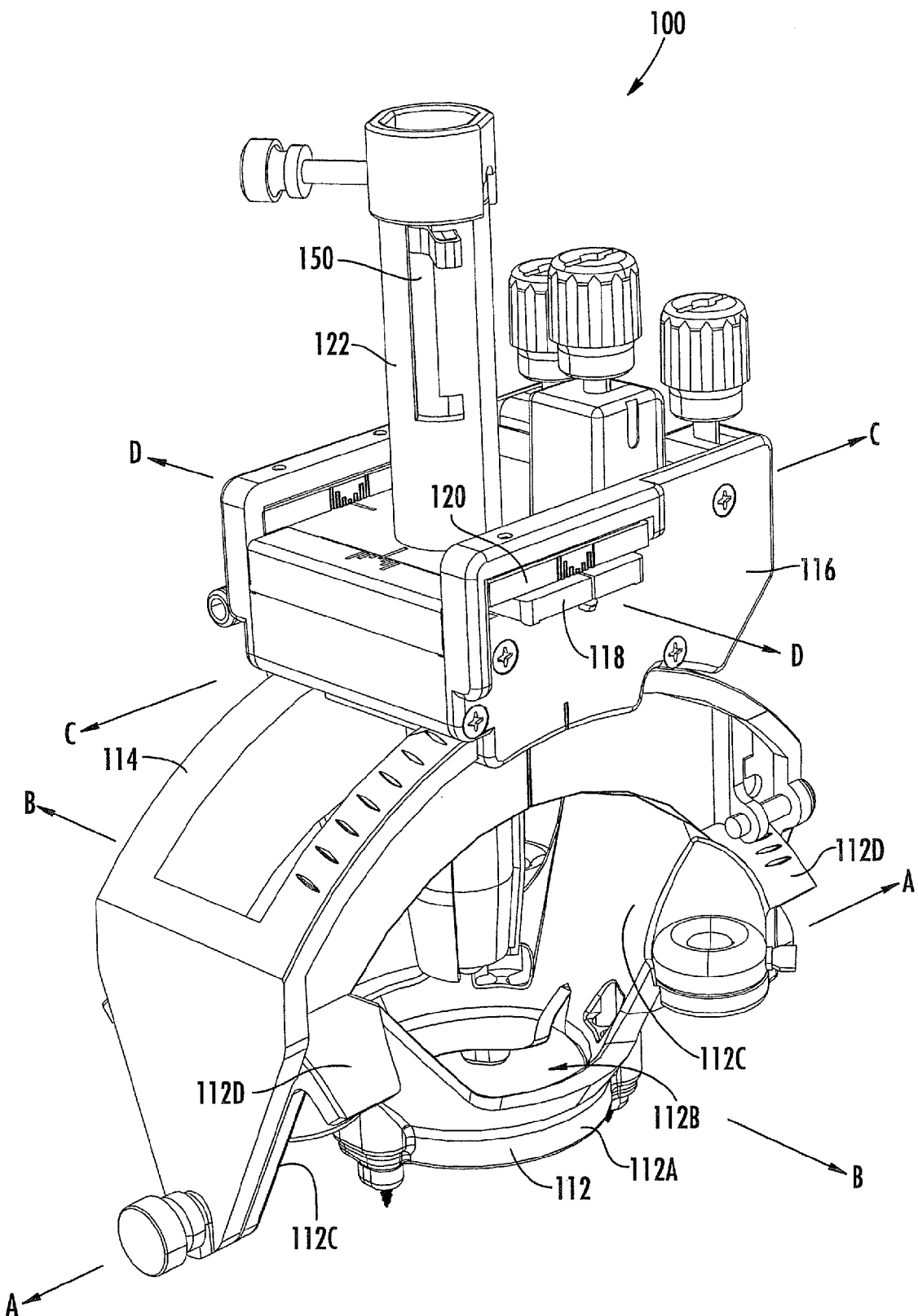
FIG. 6B is a rear perspective view of the trajectory guide apparatus of FIG. 6A.
Figure 6C:
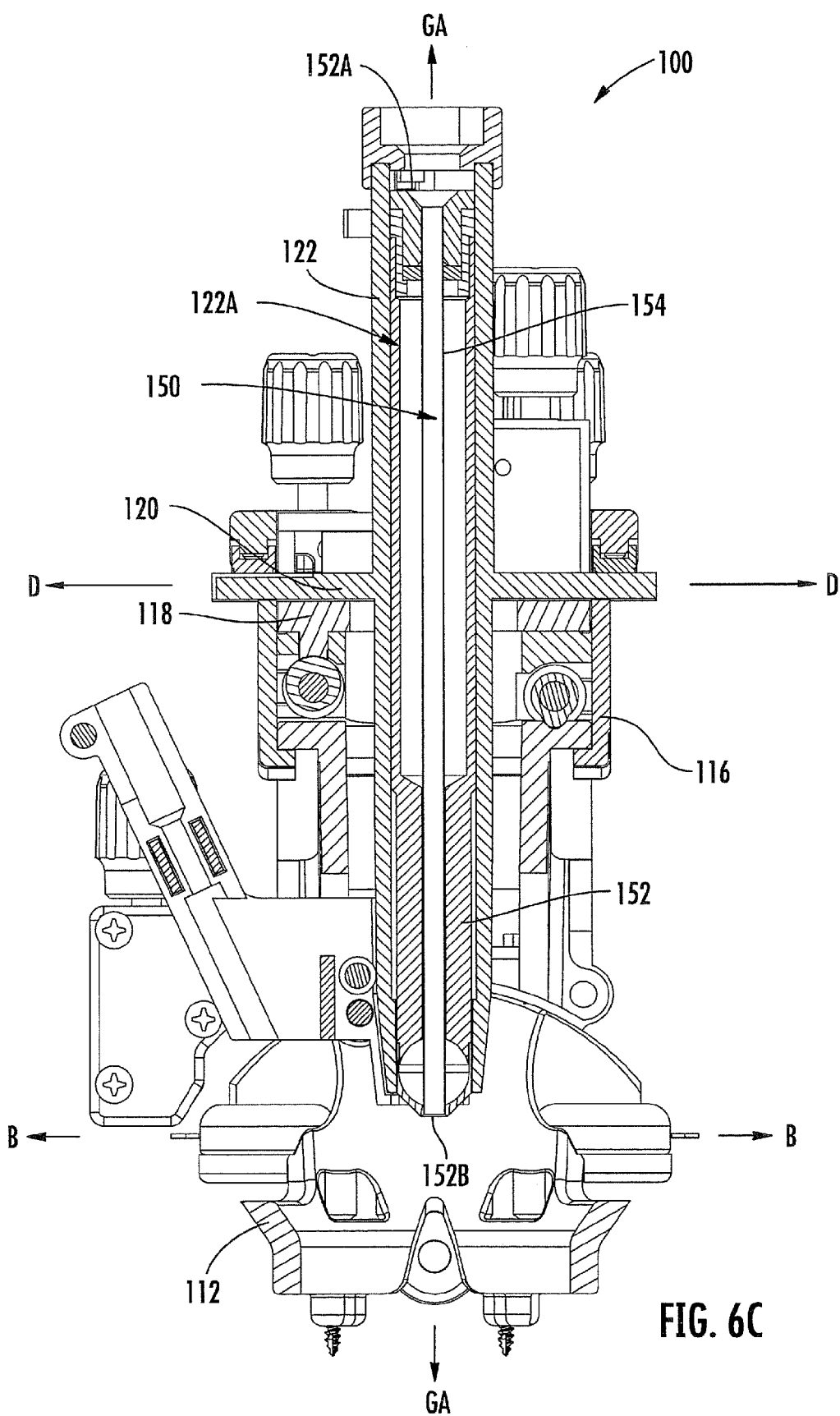
FIG. 6C is a cross-sectional view of the trajectory guide apparatus of FIG. 6A taken along the line 6C-6C of FIG. 6A.

With reference to FIGS. 6A-6C, the apparatus 100 is a frameless mount guide apparatus and includes a frame or mount assembly 110 and a targeting cannula 150. According to some embodiments, the apparatus 100 is formed entirely of MRI-compatible material(s). Although shown as a frameless mount apparatus 100, frame-based or other suitable mounting systems may also be used.

The mount assembly 110 includes a base member 112, a first arc shuttle or yoke 114, a second arc shuttle or support table 116, a first X-Y shuttle or lower moving plate 118, and a second X-Y shuttle or upper moving plate 120. The base member 112 has a lower portion 112A defining an access opening or lumen 112B. The base member 112 further includes opposed posts 112C and arcuate rails 112D. The yoke 114 is mounted on the rails 112D to translate along the curvilinear path defined by the rails 112D and thereby pivot relative to the base member 112 in a constrained arc about a transverse axis A-A. The support table 116 is mounted on the yoke 114 to translate along the curvilinear path defined by the yoke 114 and thereby pivot relative to the base member 112 in a constrained arc about a transverse axis B-B. The lower moving plate 118 is mounted on the support table 116 to selectively translate relative to the support table 116 along a transverse axis C-C in a Y-direction. The upper moving plate 120 is mounted on the support table 116 to selectively translate relative to the support table 116 along a transverse axis D-D in an X-direction.

The targeting cannula 150 includes an elongate body 152 having a distal end 152A and a proximal end 152B. A guide lumen 154 extends through the cannula 150 from end to end. The targeting cannula 150 may correspond to the guide device 5 as described above and defines a guide axis GA (FIG. 6C) that defines an approach or access path orientation or trajectory (e.g., of an interventional device inserted into the patient through the lumen 154). At least portions of the targeting cannula 150 are configured to be visible in an MRI image, thereby allowing a clinician to visualize the location and orientation of the targeting cannula. According to some embodiments, the targeting cannula 150 includes a fluid-filled stem. See, e.g., PCT Application No. PCT/US2006/045752, published as PCT Publication No. WO/2007064739 A2, the contents of which are hereby incorporated by reference. The targeting cannula 150 is mounted on the upper moving plate 120 for movement therewith. In some embodiments, a tubular targeting cannula guide member 122 is joined to the upper moving plate 120 and the targeting cannula 150 can slide up and down in a passage 122A of the targeting cannula guide member 122.

As will be appreciated from the drawings, the description herein, and the disclosures of the patent applications referenced herein, the yoke 114, support table 116, moving plate 118 and moving plate 120 can be selectively positioned in various combinations of positions on or about their respective axes A-A, B-B, C-C, D-D (FIG. 6B) to orient and position the targeting cannula 150 as desired with respect to the access opening 112B, and thereby with respect to the body B of the patient. Such adjustments can be made in any suitable manner (including manually or programmatically) using any suitable mechanisms.

When suitably mounted on the body B by the base member 112, the apparatus 100 can enable adjustment of the targeting cannula orientation/trajectory path into the body and around a pivot point (i.e., the pivot point PP) that is proximate,(e.g., over, in or below) a target entry location into the body (e.g., at a skull surface over a burr hole). This adjustment can be achieved by adjusting two separate directions along the axes A-A and B-B for pitch and roll adjustment. When such adjustments are made, the guide axis GA pivots about the pivot point PP.

Furthermore, according to some embodiments, the apparatus 100 enables X, Y offset adjustments for individually adjusting X and Y coordinates of the targeting cannula 150 relative to the access lumen 112B. The X, Y adjustments can allow for a clinician to select a parallel trajectory adjustment. Advantageously, the trajectory guide system can be configured to allow a clinician to select either a "new" trajectory or a trajectory that is parallel to a prior trajectory using one or more of the four different position adjustments provided by the apparatus 100.

The device controller 50 may be any suitable device for controlling the adjustments of the apparatus 100 to selectively adjust the orientation of the targeting cannula 150. For example, suitable device controllers are disclosed in U.S. patent application Ser. No. 12/134,412, filed Jun. 6, 2008 and U.S. patent application Ser. No. 12/237,075, filed Sep. 24, 2008 the disclosures of which are incorporated herein by reference.

The scanning apparatus 20 may be any suitable scanning or imaging apparatus. According to some embodiments and as described herein, the scanning apparatus 20 is an MRI scanner.

The controller 40 may be any suitable computer(s) or the like adapted to carry out the functions described herein. The controller 40 be integrated or distributed among one or more circuits, modules, devices or the like, which may share control of the controller 40. The user interface 45 may include a man-machine interface to enable an operator to access and control operations of the system 10. The controller 40 is operably connected to each of the display 30 and the scanning apparatus 20. The controller 40 may include a trajectory guide module 40A.

In some embodiments, the controller 40 is in communication with a graphical user interface (GUT) that allows a clinician to define a desired trajectory and/or end position on a displayed image, then can electronically convert the orientation/site input data programmatically to generate position data for the trajectory guide apparatus 100. The GUI can include an interactive tool that allows a clinician to draw, trace or otherwise select and/or identify the target treatment site and/or access path trajectory. The system 10 can then be configured to identify adjustments to the apparatus 100 that are most likely to achieve this trajectory.

In some embodiments, the user interface 45 can be configured to electronically determine the location of the targeting cannula/frameless headmount and a trajectory associated therewith. The user interface 45 can be configured to display MRI images with the projected trajectory and intersection point(s) that will be followed if the interventional/surgical device/lead is advanced using a defined position of the apparatus 100.

The guide apparatus 100 allows the operator to align the access path trajectory to an internal target site, such that the interventional/surgical device/lead, therapy, etc. will be delivered to the target site following the desired trajectory through the cranial tissue. This trajectory goes through the pivot point PP.

Figure 7:
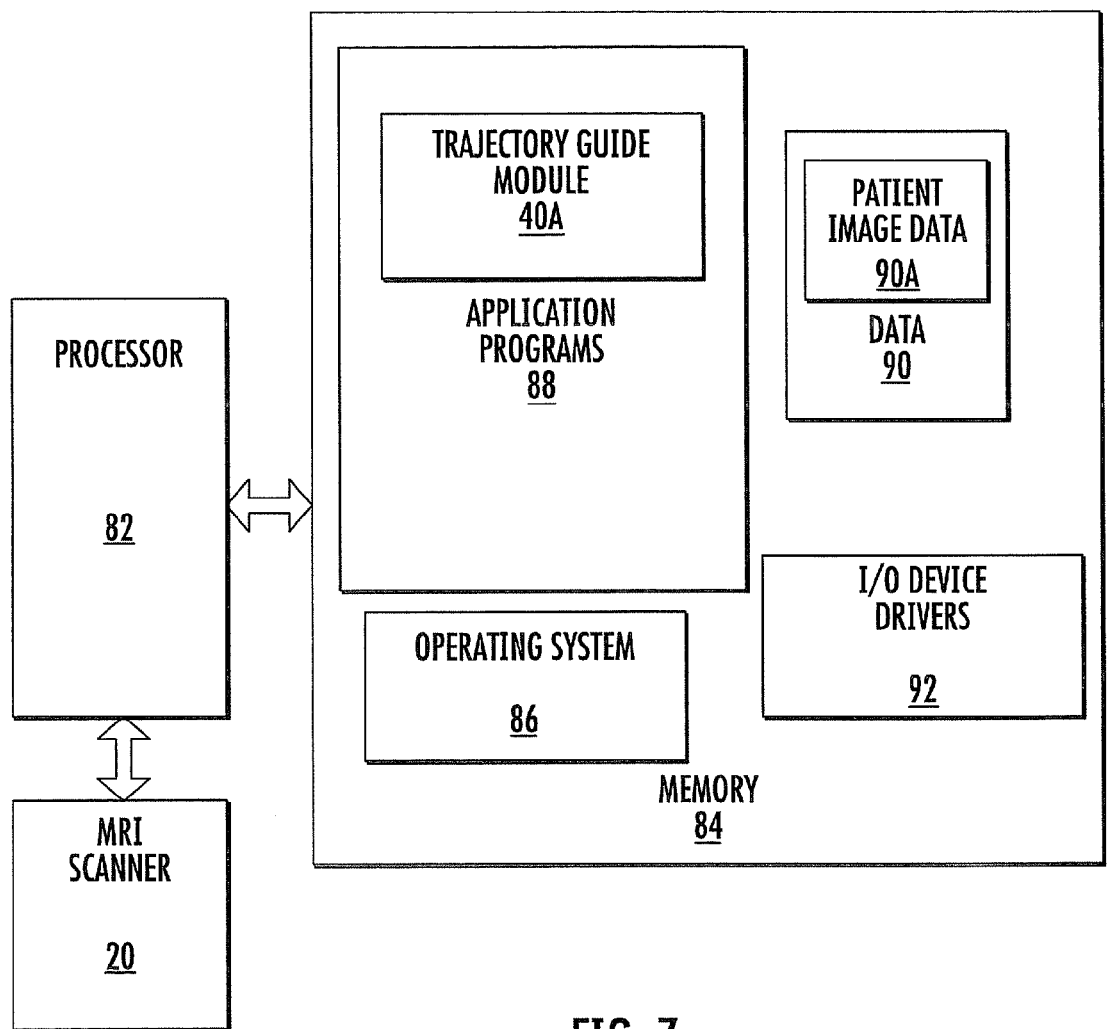
FIG. 7 is a data processing system according to embodiments of the present invention.

The system 10 (FIG. 5) can include circuits or modules that can comprise computer program code used to automatically or semi-automatically carry out operations to generate multi-dimensional visualizations during an MRI guided therapy. FIG. 7 is a schematic illustration of a circuit or data processing system 80 that can be used with the system 10. The circuits and/or data processing systems 80 data processing systems may be incorporated in a digital signal processor in any suitable device or devices. As shown in FIG. 7, the processor 82 communicates with an MRI scanner 20 and with memory 84 via an address/data bus 85. The processor 82 can be any commercially available or custom microprocessor. The memory 84 is representative of the overall hierarchy of memory devices containing the software and data used to implement the functionality of the data processing system. The memory 84 can include, but is not limited to, the following types of devices: cache, ROM, PROM, EPROM, EEPROM, flash memory, SRAM, and DRAM.

FIG. 7 illustrates that the memory 84 may include several categories of software and data used in the data processing system: the operating system 86; the application programs 88; the input/output (I/O) device drivers 92; and data 90. The data 90 can also include tool and patient-specific image data 90A. FIG. 28 also illustrates the application programs 88 can include the trajectory guide module 40A.

As will be appreciated by those of skill in the art, the operating systems 452 may be any operating system suitable for use with a data processing system, such as OS/2, AIX, DOS, OS/390 or System390 from International Business Machines Corporation, Armonk, N.Y., Windows CE, Windows NT, Windows95, Windows98, Windows2000 or other Windows versions from Microsoft Corporation, Redmond, Wash., Unix or Linux or FreeBSD, Palm OS from Palm, Inc., Mac OS from Apple Computer, LabView, or proprietary operating systems. The I/O device drivers 92 typically include software routines accessed through the operating system 86 by the application programs 88 to communicate with devices such as I/O data port(s), data storage 90 and certain memory 84 components. The application programs 88 are illustrative of the programs that implement the various features of the data processing system and can include at least one application, which supports operations according to embodiments of the present invention. Finally, the data 90 represents the static and dynamic data used by the application programs 88, the operating system 86, the I/O device drivers 92, and other software programs that may reside in the memory 84.

While the present invention is illustrated, for example, with reference to the module 40A being an application program or programs in FIG. 7, as will be appreciated by those of skill in the art, other configurations may also be utilized while still benefiting from the teachings of the present invention. For example, the module 40A and/or may also be incorporated into the operating system 86, the I/O device drivers 92 or other such logical division of the data processing system. Thus, the present invention should not be construed as limited to the configuration of FIG. 7 which is intended to encompass any configuration capable of carrying out the operations described herein. Further, one or more of modules, i.e., module 40A can communicate with or be incorporated totally or partially in other components, such as an MRI scanner.

The I/O data port can be used to transfer information between the data processing system, the MRI scanner, the tool and another computer system or a network (e.g., the Internet) or to other devices controlled by the processor. These components may be conventional components such as those used in many conventional data processing systems, which may be configured in accordance with the present invention to operate as described herein.

The following steps may be conducted in accordance with embodiments of the present invention to execute a typical surgical procedure:

1—Place the patient in an MR scanner and generate corresponding MR image data. From the MR image data, MR images are obtained of the patient's head that visualize the patient's skull, brain, fiducial markers and target region TR ROI (region of interest or target therapeutic site). The MR images can include volumetric high-resolution images of the brain.

2—To identify the target ROI, certain known anatomical landmarks can be used, i.e., reference to the AC, PC and MCP points (brain atlases give the location of different anatomies in the brain with respect to these point) and other anatomical landmarks.

3—The location of the burr hole may optionally be determined manually by placing fiducial markers on the surface of the head or programmatically by projecting the location in an image.

4—Image in the planned plane of trajectory and confirm that the trajectory is viable, i.e., that no complications with anatomically sensitive areas should occur.

5—Optically or manually mark one or more desired locations to drill the burr hole.

6—Drill the burr or patient access hole.

7—Fix the burr hole ring (where used).

8—Fix the guide apparatus that defines the guide axis. The guide apparatus may include a targeting cannula as described herein.

9—Conduct guide device alignment procedure as described herein to align the guide axis GA with the planned trajectory line PTL.

10—Advance interventional device (e.g., probe, lead or the like) through the targeting cannula, into the head and to the target.

In embodiments as described above with reference to FIGS. 1A-4, the guide axis GA is determined by reference to a fixed pivot point PP, which is also located on the planned trajectory line PTL. According to further embodiments, the guide axis GA may be determined without reference to a pivot point and, in some embodiments, the guide axis may not be pivotable. Exemplary embodiments will now be described.

Systems and method according to further embodiments of the present invention will be described with reference to FIGS. 8A-9C. These systems and methods may correspond to the systems and methods described above with reference to FIGS. 1A-4 except as discussed below. A body B of a patient (as shown, the patient's head) is again shown in FIGS. 8A-9C. FIGS. 8A and 9A are perspective views, FIGS. 8B and 9B are top views and FIGS. 8C and 9C are side views. The order of at least certain of the steps described below may be rearranged and some of the steps and apparatus may be omitted or modified in accordance with further embodiments of the invention.

Referring to FIGS. 8A-8C, the planned trajectory line PTL may be determined as described above by defining a line extending through the target point TP and a selected reference point RP. According to some embodiments, the reference point RP is an entry location point EP that is at or proximate the location where the planned trajectory line PTL intersects an entry surface of the body B. The visualization plane VP is selected and scanned as described above.

In accordance with some embodiments, the guide axis GA is determined by tracking at least two different points on the guide device 5. According to some embodiments, two axially spaced apart acquisition planes (AP1 and AP2) may be selected, the planes AP1 and AP2 being relatively oriented and positioned so that they intersect the guide device 5 at different points (a first guide component point GCP1 and a second guide component point GCP2, respectively) along the guide axis GA. Scans are taken along each acquisition plane AP1, AP2 to track the position of the guide device 5 in each plane AP1, AP2. From these two points, the orientation and position of the guide axis GA is determined. According to some embodiments, the guide device 5 is alternatively or additionally tracked using a different tracking device or devices such as LEDs, microcoils, or other suitable devices.

Using the information from the scan(s) of the acquisition planes AP1, AP2, the orientation of the guide axis GA is programmatically determined. The controller 40 extrapolates the guide axis GA and determines the location GPP of the guide axis' GA intersection with the visualization plane VP. According to some embodiments, the point of intersection GPP between the guide axis GA and the visualization plane VP is not a point on the guide device 5. The controller 40 may determine or derive the location of the guide axis projected point GPP by mathematical calculation and/or any other suitable method.

The controller 40 can provide a displayed image as described above including representations of the sighting point (e.g., the target point TP) and the guide axis projected point GPP. The display and tracking may be used by the operator to align the guide axis GA with the planned trajectory line PTL as described above. FIGS. 9A-C are views corresponding to the views of FIGS. 8A-C, respectively, wherein the guide apparatus 5 is aligned with the planned trajectory line PTL.

Figure 10:
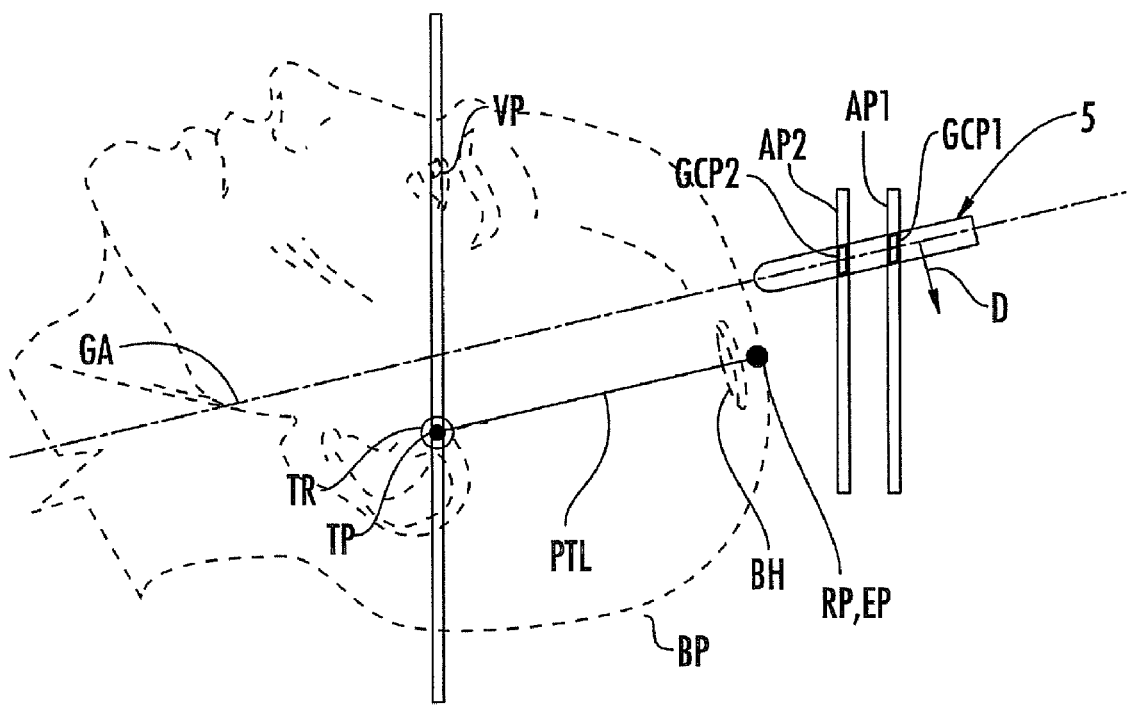
FIG. 10 is a schematic side view of a portion of a patient body and logical elements associated with methods and systems according to further embodiments of the present invention wherein a guide device thereof is oriented in a first, non-aligned position.

In the methods as just described, the planned trajectory line PTL and the guide axis GA may not necessarily share a point (such as the pivot point PP) unless and until the planned trajectory line PTL and the guide axis GA are aligned. For example, according to some embodiments, the guide axis GA is translated (in the X-Y plane) relative to the planned trajectory line PTL by adjusting the setting(s) of one or both of the moving plates 118, 120. In some embodiments, the orientation of the guide axis GA can also be adjusted by pivoting the guide axis GA about a pivot point (e.g., located at the reference point RP). For example, with reference to FIG. 10, the guide device 5 may initially be positioned and oriented relative to the patient body B such that the guide axis GA is offset from the planned trajectory line PTL. In this case, the guide axis GA does not intersect the reference point RP. As indicated by the translation direction arrow D, the guide device 5 can be linearly translated in an X and/or Y direction relative to the patient body B until the guide axis GA intersects the reference point RP. If necessary, the orientation of the guide device 5 can be adjusted to bring the guide axis GA into alignment with the planned trajectory line PTL. In some embodiments, the direction D is substantially perpendicular to the guide axis GA.

In some embodiments, the system 10 can include one or more software modules that can automate or carry out aspects of the invention. The modules can include data processing systems and computer program products in accordance with embodiments of the present invention.

Methods, systems and computer program products in accordance with the present invention may be used with apparatus and methods as described in one or more of the following patent applications: U.S. patent application Ser. No. 12/134,412, filed Jun. 6, 2008; U.S. Provisional Patent Application No. 60/974,821, filed Sep. 24, 2007; U.S. patent application Ser. No. 12/236,950, filed Sep. 24, 2008; U.S. patent application Ser. No. 12/236,854 filed Sep. 24, 2008; and U.S. patent application Ser. No. 12/236,621, filed Sep. 24, 2008; and PCT Application No. PCT/US2006/045752, published as PCT Publication No. WO/2007064739 A2.

According to some embodiments, instrumentation and equipment are inserted through the targeting cannula to execute a diagnostic and/or surgical procedure. According to some embodiments, the procedure includes a deep brain stimulation procedure wherein one or more electrical leads are implanted in a patient's brain. The apparatus described herein serves to establish the trajectory for installing the lead or leads or other interventional devices such as, for example, but not limited to, ablation probes, injection catheters and the like.

Some embodiments can be configured to deliver tools or therapies that stimulate a desired region of the sympathetic nerve chain. Other uses inside or outside the brain include stem cell placement, gene therapy or drug delivery for treating physiological conditions. Some embodiments can be used to treat tumors or biopsy tissue.

In some embodiments the interventional tools can be configured to facilitate high resolution imaging via integral imaging coils (receive antennas), and/or the interventional tools can be configured to stimulate local tissue, which can facilitate confirmation of proper location by generating a physiologic feedback (observed physical reaction or via fMRI).

Some embodiments can be used to deliver bions, stem cells or other target cells to site-specific regions in the body, such as neurological target and the like. In some embodiments, the systems deliver stem cells and/or other cardio-rebuilding cells or products into cardiac tissue, such as a heart wall via a minimally invasive MRI guided procedure, while the heart is beating (i.e., not requiring a non-beating heart with the patient on a heart-lung machine). Examples of known stimulation treatments and/or target body regions are described in U.S. Pat. Nos. 6,708,064; 6,438,423; 6,356,786; 6,526,318; 6,405,079; 6,167,311; 6539,263; 6,609,030 and 6,050,992, the contents of which are hereby incorporated by reference as if recited in full herein.

Further methods and apparatus may be employed along as part of or along with the methods and apparatus disclosed herein. According to some embodiments, an alignment procedure as described herein can be executed as part of a procedure as disclosed in U.S. patent application Ser. No. 12/236,950, filed Sep. 24, 2008, U.S. patent application Ser. No. 12/236,621, filed Sep. 24, 2008, the disclosures of which are incorporated herein by reference.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims. The invention is defined by the following claims, with equivalents of the claims to be included therein.

That which is claimed is:

1. A method for positioning a guide device for placement of an interventional object in a body, the guide device having a guide axis, the method comprising:
   determining a target point in the body and a reference point, wherein the target point and the reference point define a planned trajectory line (PTL) extending through each;
   determining a visualization plane, wherein the PTL intersects the visualization plane at a sighting point;
   mounting the guide device relative to the body to move with respect to the PTL, wherein the guide device does not intersect the visualization plane;
   acquiring at least one MRI scan along the visualization plane;
   determining an acquisition plane, wherein the guide device intersects the acquisition plane;
   tracking a position of the guide device in the acquisition plane and determining therefrom a corresponding position and/or orientation of the guide axis, wherein tracking the position of the guide device in the acquisition plane includes acquiring at least one MRI scan along the acquisition plane;
   determining a point of intersection (GPP) between the guide axis and the visualization plane; and
   aligning the GPP with the sighting point in the visualization plane.

2. The method of claim 1 wherein the reference point is a pivot point, and mounting the guide device includes mounting the guide device relative to the body to pivot the guide axis about the pivot point.

3. The method of claim 1 wherein the target point is located in a brain of the body, the method including inserting an interventional object into the brain along the PTL to a position adjacent the target point.

4. A method for positioning a guide device for placement of an interventional object in a body, the guide device having a guide axis, the method comprising:
   determining a target point in the body and a pivot point, wherein the target point and the pivot point define a planned trajectory line (PTL) extending through each;
   determining a visualization plane, wherein the PTL intersects the visualization plane at a sighting point, and wherein the sighting point is located on a segment of the PTL on a side of the pivot point proximate the target point;
   mounting the guide device relative to the body to pivot about the pivot point with respect to the PTL;
   acquiring at least one MRI scan along the visualization plane;
   determining an acquisition plane, wherein the guide device intersects the acquisition plane;
   tracking a position of the guide device in the acquisition plane and determining therefrom a corresponding position and/or orientation of the guide axis, wherein tracking the position of the guide device in the acquisition plane includes acquiring at least one MRI scan along the acquisition plane;
   determining a point of intersection (GPP) between the guide axis and the visualization plane; and
   aligning the GPP with the sighting point in the visualization plane.

5. The method of claim 4 wherein the sighting point is substantially coincident with the target point.

6. A method for positioning a guide device for placement of an interventional object in a body, the guide device having a guide axis, the method comprising:
   determining a target point in the body and a reference point, wherein the target point and the reference point define a planned trajectory line (PTL) extending through each;
   determining a visualization plane, wherein the PTL intersects the visualization plane at a sighting point, and wherein the sighting point is located within the body;
   mounting the guide device relative to the body to move with respect to the PTL;
   acquiring at least one MRI scan along the visualization plane;
   determining an acquisition plane, wherein the guide device intersects the acquisition plane;
   tracking a position of the guide device in the acquisition plane and determining therefrom a corresponding position and/or orientation of the guide axis, wherein tracking the position of the guide device in the acquisition plane includes acquiring at least one MRI scan along the acquisition plane;
   determining a point of intersection (GPP) between the guide axis and the visualization plane; and
   aligning the GPP with the sighting point in the visualization plane.

7. The method of claim 6 wherein the sighting point is substantially coincident with the target point.

8. The method of claim 6 wherein the reference point is an entry point located at or proximate a point of intersection between the PTL and an entry surface of the body.

9. The method of claim 6 wherein the reference point is a pivot point and mounting the guide device includes mounting the guide device relative to the body to pivot about the pivot point.

10. The method of claim 6 including programmatically determining the GPP using the position of the guide device in the acquisition plane.

11. A method for positioning a guide device for placement of an interventional object in a body, the guide device having a guide axis, the method comprising:
    determining a target point in the body and a reference point, wherein the target point and the reference point define a planned trajectory line (PTL) extending through each;
    determining a visualization plane, wherein the PTL intersects the visualization plane at a sighting point, and wherein the PTL is orthogonal to the visualization plane;
    mounting the guide device relative to the body to move with respect to the PTL, wherein the guide device does not intersect the visualization plane;
    acquiring at least one MRI scan along the visualization plane;
    determining an acquisition plane, wherein the guide device intersects the acquisition plane;
    tracking a position of the guide device in the acquisition plane and determining therefrom a corresponding position and/or orientation of the guide axis, wherein tracking the position of the guide device in the acquisition plane includes acquiring at least one MRI scan along the acquisition plane;
determining a point of intersection (GPP) between the guide axis and the visualization plane; and
aligning the GPP with the sighting point in the visualization plane.

12. The method of claim 11 wherein the reference point is a pivot point and mounting the guide device includes mounting the guide device relative to the body to pivot about the pivot point.

13. A method for positioning a guide device for placement of an interventional object in a body, the guide device having a guide axis, the method comprising:
determining a target point in the body and a reference point, wherein the target point and the reference point define a planned trajectory line (PTL) extending through each;
determining a visualization plane, wherein the PTL intersects the visualization plane at a sighting point;
mounting the guide device relative to the body to translate the guide axis with respect to the PTL;
acquiring at least one MRI scan along the visualization plane;
determining an acquisition plane, wherein the guide device intersects the acquisition plane;
tracking a position of the guide device in the acquisition plane and determining therefrom a corresponding position and/or orientation of the guide axis, wherein tracking the position of the guide device in the acquisition plane includes acquiring at least one MRI scan along the acquisition plane;
determining a point of intersection (GPP) between the guide axis and the visualization plane; and
aligning the GPP with the sighting point in the visualization plane.

* * * * *